United States Patent [19]

Haskell et al.

[11] 4,278,681

[45] Jul. 14, 1981

[54] ANTIBACTERIAL AMIDE COMPOUNDS AND MEANS FOR USING THE SAME

[75] Inventors: Theodore H. Haskell, Ann Arbor; Marland P. Hutt, Jr., Saline; Ernest D. Nicolaides, Ann Arbor; Peter W. K. Woo, Ann Arbor; Gin G. Huang, Ann Arbor, all of Mich.

[73] Assignee: Warner-Lambert Co., Morris Plains, N.J.

[21] Appl. No.: 112,657

[22] Filed: Jan. 31, 1980

Related U.S. Application Data

[63] Continuation-in-part of Ser. No. 20,000, Mar. 12, 1979, abandoned.

[51] Int. Cl.$^3$ .................... A61K 31/455; C07D 499/68
[52] U.S. Cl. .................... 424/266; 260/239.1; 546/298
[58] Field of Search .................... 424/266; 260/239.1

[56] References Cited

U.S. PATENT DOCUMENTS

| | | | |
|---|---|---|---|
| 3,873,523 | 3/1975 | Doub et al. | 260/239.1 |
| 3,954,734 | 5/1976 | Doub et al. | 260/239.1 |
| 4,053,470 | 10/1977 | Doub et al. | 260/239.1 |
| 4,092,309 | 5/1978 | Mich | 260/239.1 |

*Primary Examiner*—Natalie Trousof
*Assistant Examiner*—Vera C. Clarke
*Attorney, Agent, or Firm*—Stephen Raines

[57] ABSTRACT

Novel organic amide compounds which are N-[6-[(acylaminoacylamino or aminoacylamino)phenyl]-1,2-dihydro-2-oxonicotinyl] penicillin compounds having broad spectrum antibacterial utility are provided by (a) reacting the free amino acid of the appropriate penicillin or the acid salt or silylated derivative or complex thereof with a reactive derivative of the corresponding N-6-[(acylaminoacylamino or aminoacylamino)-phenyl]-1,2-dihydro-2-oxonicotinic acid or (b) reacting the free amino acid 6-aminopenicillanic acid or a related compound or the acid salt or silylated derivative thereof with a reactive derivative of the corresponding D-N-[6-[(acylaminoacylamino or aminoacylamino) phenyl]-1,2-dihydro-2-oxonicotinyl]-2-substituted glycine. Pharmaceutical compositions containing said compounds and methods for treating infections using said compositions are also disclosed.

39 Claims, No Drawings

ANTIBACTERIAL AMIDE COMPOUNDS AND MEANS FOR USING THE SAME

This is a continuation-in-part of copending U.S. application, Ser. No. 20,000, filed Mar. 12, 1979, now abandoned.

SUMMARY AND DETAILED DESCRIPTION

The present invention relates to novel chemical compounds that are useful as pharmacological agents and to methods for their production. More particularly, the invention relates to novel organic amide compounds having the formula

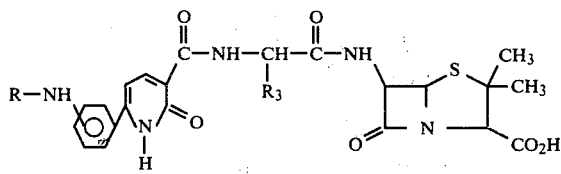

and pharmaceutically acceptable salts thereof; wherein R is

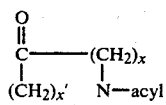

or $R_1$—[$NR_4$-acyl]$_n$; x is an integer from one to five, x' is zero, one or two; $R_1$ is hydrogen, lower alkyl, benzyl, or

wherein $R_2$ is hydrogen, amino or a lower alkyl group of from one to four carbon atoms, optionally substituted by from one to three chlorine or fluorine atoms; $R_4$ is hydrogen or lower alkyl; N-acyl is an aminoacyl moiety derived from a carboxylic acid of from two to ten carbon atoms optionally substituted by from one to three of the following groups, formamido, lower alkylamido, hydroxyl,

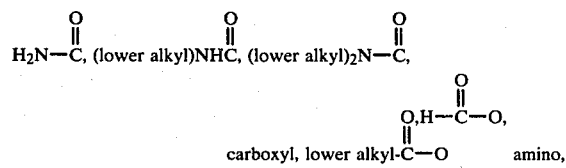

carbamido, carbonyl oxygen, lower alkoxy, lower alkylthio, or sulfonic acid; $R_3$ is phenyl, 4-hydroxyphenyl, 2-thienyl or cyclohexa-1,4-dien-1-yl and n is an integer of from one to four. When n is two to four, the acyl group may be the same or different. When the acyl group is substituted by more than one group, the substituents may be the same or different.

Included within the above definition for N-acyl are cyclic structures incorporating the nitrogen atom by displacement of the hydrogen atom, such as the pyroglutamyl group, prolyl group, etc.

The carbon atoms may be part of a configuration which is classified as as aliphatic, olefinic or aromatic grouping or mixture of both, such as phenethyl group.

The preferred compounds are those wherein R-NH is in the p position and is an optically active $R_1$ aminoacyl fragment which is in the L form. The most preferred compounds are those wherein N-acyl is L-alanyl, L-glutaminyl, L-4-hydroxyprolyl, L-prolyl, L-pyroglutamyl, $\gamma$-aminobutyryl, $\beta$-alanyl or L-valyl: $R_2$ is a lower alkyl group of from one to four carbon atoms and $R_3$ is phenyl or p-hydroxyphenyl and pharmaceutically acceptable salts thereof.

Lower alkyl, where not specifically defined, is defined as a hydrocarbon fragment of from one to six carbon atoms. Lower alkoxy is equivalent to "lower alkyl-O-".

In accordance with the invention the foregoing amide compounds having the formula

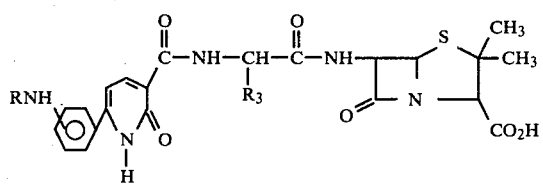

and pharmaceutically acceptable salts thereof wherein R and $R_3$ are as previously defined are produced by reacting a compound of the formula

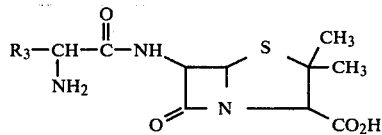

or the basic salt, silylated derivative (preferably the disilylated) or complex (preferably the dimethylsulfoxide) thereof with a reactive derivative of a 1,2-dihydro-2-oxonicotinic acid compound having the formula

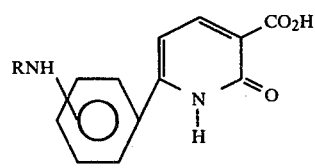

or its acid addition salt, wherein R and $R_3$ are as previously defined.

Some examples of reactive derivatives of the 6-(substituted)-1,2-dihydro-2-oxonicotinic acid compound suitable for the reaction are the acid halides (especially the acid chloride), the imidazolide, mixed anhydrides (especially those from an alkyl chloroformate such as methyl, ethyl, and isobutyl chloroformate or pivaloyl chloride), and activated esters such as the pentachlorophenyl ester and N-hydroxysuccinimide ester.

The reactants are normally employed in approximate equimolar quantities, although an excess of either (oxonicotinic acid compound or amino acid compound) can be used if desired. The reaction can be carried out in any of a number of unreactive solvents. When using a silylated derivative for the reaction the solvent should be anhydrous and may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, when using the penicillin compounds in the free acid or salt form, aqueous solutions may be used for acylation with an acid halide or mixed anhydride under normal Schotten-Baumann conditions. The duration and temperature of the reaction are not critical. Temperatures in the range from −30° to +30° C. are commonly used for reaction times ranging from a few hours up to a day or more. The product may be isolated in any suitable way as the free acid or as a salt by appropriate adjustment of the pH.

The reactive derivative of 6-(substituted)-1,2-dihydro-2-oxonicotinic acid compounds and acid-addition salts which are required as starting materials in the foregoing process can be prepared according to any of a variety of methods.

A 6-(substituted)-1,2-dihydro-2-oxonicotinic acid may be converted to its acid chloride utilizing thionyl chloride, its mixed anhydride utilizing ethyl chloroformate, its pentachlorophenyl ester by esterification with pentachlorophenol and its imidazolide by reacting the acid with 1,1′-carbonyldiimidazole.

Compounds of the formula

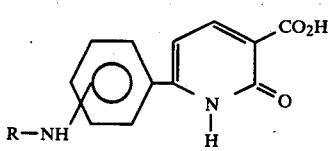

wherein R is as previously defined except wherein $R_1$ is hydrogen are prepared by acylation of a compound of the formula

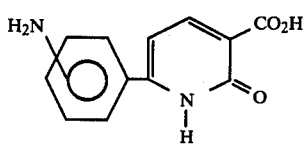

by a compound of the formula

 R—OH wherein R is as previously defined except where $R_1$ is hydrogen.

The compound of the formula

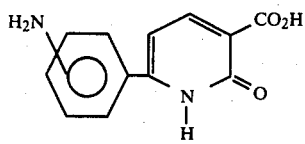

is prepared by hydrolyzing a compound of the formula

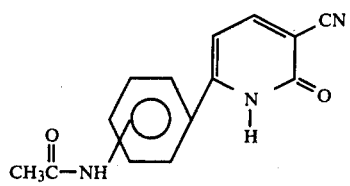

which is in turn prepared by coupling a compound of the formula

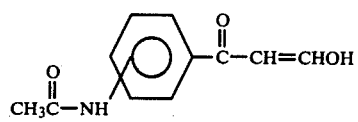

with 2-cyanoacetamide.

The compound of the formula

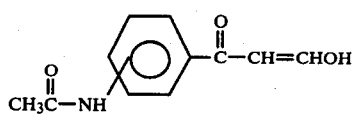

is prepared by formylating a compound of the formula

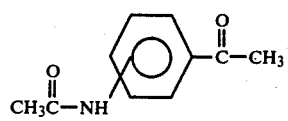

The silylated amino acid starting materials can be prepared by reacting an amino acid of the formula

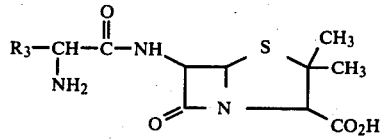

or a salt thereof wherein $R_3$ is as previously defined in anhydrous form with either one or two equivalents of a tri(lower alkyl)silyl chloride in the presence of triethylamine. The preferred silylating agents are trimethylsilyl chloride and dimethyl dichlorosilane. When two equivalents of the silylating agent are used, both the amino and the carboxyl group become silylated. When one equivalent is used, only the carboxyl group is silylated. Both the mono- and disilylated products are fully reactive with the activated acids. The disilylated product is preferred over the monosilylated product as a starting material. After acylation the silyl groups are easily removed by treatment with water.

Also in accordance with the invention, the compounds of this invention may be produced by reacting a free amino acid of the formula

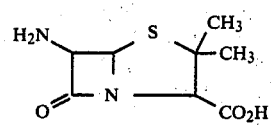

or the corresponding acid salt or silylated derivative thereof with a reactive derivative of D-N-[6-(substituted)-1,2-dihydro-2-oxonicotinyl]-2-substituted glycine having the formula

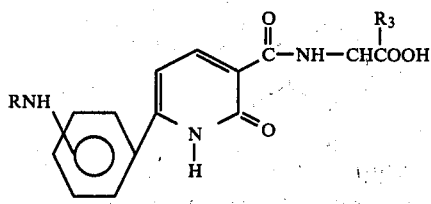

or its acid addition salts where R and $R_3$ have the aforementioned significance.

Some examples of reactive derivatives of the D-N-(1,2-dihydro-2-oxonicotinyl)-2-substituted glycine compounds suitable for the reaction are the acid halides, mixed anhydrides (especially those formed from an alkyl chloroformate such as ethyl chloroformate and isobutyl chloroformate), and activated esters such as the pentachlorophenyl ester and N-hydroxysuccinimide ester. Since raceminzation is more likely with the acid halide, the other forms are generally preferred. The reactants are normally employed in approximate equimolar quantities, although an excess of either (oxonicotinic acid compound or amino acid compound) can be used if desired. The reaction can be carried out in any of a number of unreactive solvents. When using the silylated derivative for the reaction the solvent should be anhydrous and may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, 6-aminopenicillanic acid may be reacted with an acid chloride or mixed anhydride in the free acid or salt form using aqueous solutions under normal Schotten-Baumann conditions. The duration and temperature of the reaction are not critical. Temperatures in the range from $-30°$ to $+30°$ C. are commonly used for reaction times ranging from a few hours up to a day or more. The product may be isolated in any suitable way as the free acid or as a salt by appropriate adjustment of the pH.

The reactive derivative of D-N-[6-(substituted)-1,2-dihydro-2-oxonicotinyl]-2-substituted glycines or their acid-addition salts which are required as starting materials in the foregoing process can be prepared by methods illustrated in greater detail hereinafter.

D-N-[6-substituted)]-1,2-dihydro-2-oxonicotinyl)-2-substituted glycine compounds may be prepared by reacting the corresponding reactive derivative of 6-(substituted)-1,2-dihydro-2-oxonicotinic acid, such as acid chloride, with the appropriate D-N-(trimethylsilyl)-2-substituted glycine, trimethylsilyl ester in the presence of triethylamine followed by hydrolysis.

The silylated amino acid starting materials can be prepared by reacting an anhydrous compound of the formula

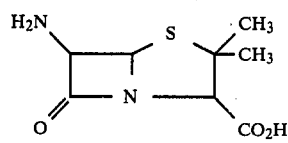

with a hexaalkyldisilazane. The preferred silylating agent is hexamethyldisilazane. Only the carboxyl group is silylated under the conditions used (e.g., 2-hour reflux in dichloromethane). After acylation, the silyl group is easily removed by treatment with water.

The free acids of the invention form carboxylate salts with any of a variety of inorganic and organic bases. Pharmaceutically acceptable carboxylate salts are formed by reacting the free acids with such bases as sodium hydroxide, sodium carbonate, sodium bicarbonate, sodium 2-ethylhexanoate, potassium hydroxide, potassium carbonate, potassium 2-ethylhexanoate, calcium hydroxide, ethylamine, 2-hydroxyethylamine, and procaine. Preferred carboxylate salt forms are the alkali metal salts. The carboxylate salts are converted to the free acids by acidification. The free acids and their carboxylate salts usually differ somewhat in solubility properties but, in general, are otherwise equivalent for the purposes of the invention. In addition, certain of the compounds of the invention can exist in the form of an acid-addition salt Pharmaceutically acceptable salts are formed by reaction of the free base of a carboxylate salt with any of a number of inorganic and organic acids, including hydrochloric, sulfuric, nitric, phosphoric, acetic, benzoic, citric, maleic, malic, tartaric, succinic, gluconic, ascorbic, sulfamic, pamoic, methanesulfonic, benzenesulfonic and related acids.

When forming salts certain compounds may form mono, di, or tri, etc., salts. All of these compounds are intended to be equivalent for the purposes of the invention and are intended to fall within the scope of the invention.

The compounds of the invention can exist in anhydrous form, as well as in solvated, including hydrated, forms. In general, the hydrated forms and the solvated forms with pharmaceutically acceptable solvents are equivalent to the anhydrous or unsolvated forms for the purposes of the invention.

The pyridone segment of the compounds of this invention may be capable of undergoing keto-enol tautomerism to give 2-hydroxypyridines. Such a tautomer is equivalent to the pyridones for the purposes of the inventions and are included within the above shown structures.

The compounds of the present invention can exist in various stereoisomeric forms. More specifically, the newly introduced amino acid fragments of the compounds may be in the form of the D-isomer, L-isomer or a mixture thereof [DL-mixture (partial or complete racemization)]. The invention is intended to include all of the isomeric forms and mixtures thereof. Even when a specific form is cited, small amounts of its stereoisomer may be present, since racemization may occur during the various steps in preparing the compound.

The compounds of the invention are new chemical compounds that are used as pharmacological agents and especially as broad spectrum antibacterial agents. They are active in vitro against strains of both gram-positive and gram-negative bacteria. The activity of the compounds is illustrated by the results shown in the table for certain of the preferred compounds.

Thus, the compounds of this invention and their non-toxic pharmaceutically acceptable salts are highly useful as broad spectrum antibiotics in mammals when administered in amounts ranging from about 5 mg to about 100 mg per kg of body weight per day. A preferred dosage regimen for optimum results would be from about 10 mg to about 50 mg per kg of body weight per day, and such dosage units are employed that a total of about 700 mg to about 3500 mg of active ingredient for a subject of about 70 kg body weight are administered in a 24 hour period in an appropriate pharmaceutical composition.

While the compounds of this invention may be administered orally in the form of tablets, capsules, syrups, etc., the preferred route of administration is parenterally for treating systemic infections.

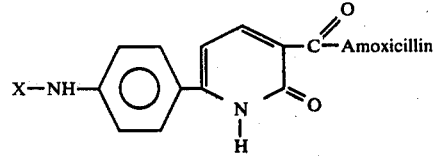

ACTIVITY TABLE

Minimal Inhibitory Concentration by Microtitration (μg/ml)
Dilution in TSB (Trypticase soy broth).

| Side Chain X | Serratia marcescens IMM-16 | Pseudomonas aeruginosa UI-18 | Pseudomonas aeruginosa BRK 12-4-4 | Enterobacter cloacae IMM-11 | Klebsiella pneumoniae MGH-2 |
|---|---|---|---|---|---|
| AcNH—CH(CH₃)—C(=O)— L | 3.1 | 0.8 | 1.6 | 1.6 | 3.1 |
| AcNH—CH₂CH₂CH₂C(=O)— | 3.1 | 1.6 | 3.1 | 6.3 | 3.1 |
| N-Ac pyrrolidine-C(=O)— L | 6.3 | 1.6 | 1.6 | 6.3 | 12.5 |
| NH₂C(=O)—CH₂CH₂—CH(NHAc)—C(=O)— L | 3.1 | 1.6 | 3.1 | 3.1 | 12.5 |
| HO-pyrrolidine(N-Ac)-C(=O)— L | 6.3 | 1.6 | 3.1 | 3.1 | 12.5 |
| HC(=O)—NH—CH(CH₃)—C(=O)— L | 3.1 | 1.6 | 1.6 | 3.1 | 6.3 |
| AcNH—CH(CH₃)—C(=O)—NH—CH(CH₃)—C(=O)— L,L | 6.3 | 3.1 | 6.3 | 12.5 | 25 |
| 2-oxo-pyrrolidine-C(=O)— L | 3.1 | 3.1 | 1.6 | 1.6 | 6.3 |
| NH₂C(=O)—NH—CH(CH₃)—C(=O)— L | 3.1 | 1.6 | 1.6 | 6.3 | 6.3 |
| AcO-pyrrolidine(N-Ac)-C(=O)— L | 6.3 | 1.6 | 1.6 | 6.3 | 12.5 |
| O=pyrrolidine(N-Ac)-C(=O)— L | 12.5 | 3.1 | 6.3 | 12.5 | 25 |

-continued

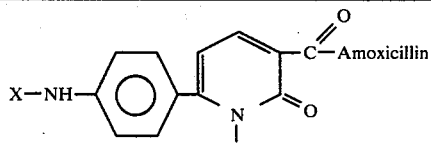

ACTIVITY TABLE

Minimal Inhibitory Concentration by Microtitration (μg/ml) Dilution in TSB (Trypticase soy broth).

| Side Chain X | Serratia marcescens IMM-16 | Pseudomonas aeruginosa UI-18 | Pseudomonas aeruginosa BRK 12-4-4 | Enterobacter cloacae IMM-11 | Klebsiella pneumoniae MGH-2 |
|---|---|---|---|---|---|
| AcO-pyrrolidine-C(O)- D-allo (N-Ac) | 12.5 | 3.1 | 6.3 | 12.5 | 25 |
| CH₃O-pyrrolidine-C(O)- L (N-Ac) | 12.5 | 3.1 | 6.3 | 12.5 | 25 |
| dihydropyrrole-C(O)- DL (N-Ac) | 12.5 | 3.1 | 3.1 | 6.3 | 12.5 |
| HCO-O-pyrrolidine-C(O)- L (N-Ac) | 6.3 | 0.8 | 0.8 | 1.6 | 6.3 |
| EtCO-O-pyrrolidine-C(O)- L (N-Ac) | 6.3 | 1.6 | 3.1 | 6.3 | 12.5 |
| 5-oxo-pyrrolidine-C(O)- L (N-CH₃) | 6.3 | 0.8 | 1.6 | 3.1 | 6.3 |
| AcNH(CH₂)₄CH(NHAc)-C(O)- L | 50 | 6.3 | 6.3 | 12.5 | 25 |
| 2-oxopyrrolidin-1-yl-CH₂C(O)- | 6.3 | 3.1 | 3.1 | 3.1 | 6.3 |

In the present invention the term "pharmaceutical composition" is defined as a finished pharmaceutical that may be administered directly or a pharmaceutical which water is added to prior to use in order to form a satisfactory product for administration. The pharmaceutical compositions to be employed parenterally are generally supplied in a dry, sterile form having about 50 mg to about 1000 mg of active compound per vial. The vial may also contain other active ingredients, buffers, salts, etc. The sterile material in the vial is dissolved in water for injection at the time of use. Oral preparations would also have from about 50 mg to about 1000 mg of active compound per unit dose form.

The invention is illustrated by the following examples.

EXAMPLE 1

N-[6-[4-(N-acetyl-L-alanylamino)phenyl]-1,2-dihydro-2-oxonicotinyl]amoxicillin.

A suspension of 330 g (6.1 mol) of sodium methoxide, 3 l of tetrahydrofuran, and 2.5 l of ether was stirred at room temperature and a suspension of 490 g (2.77 mol)

of 4-(acetylamino)acetophenone, 416 g (5.54 mol) of ethyl formate, and 3 l of tetrahydrofuran was added over a period of 1 hr. The suspension was stirred at room temperature overnight under nitrogen. The precipitate was allowed to settle and the solvent drawn off with a filter candle. Another 3 l of tetrahydrofuran was added and the solvent again removed by filter candle.

Water (9 l) was added to the residue and the pH was adjusted to 9.0 with glacial acetic acid and 388 g (4.6 mol) of 2-cyanoacetamide was added. The mixture was warmed to 90°* on a steam bath while allowing the residual tetrahydrofuran and ether to escape. The system was fitted with a condenser and heated at this temperature overnight. The suspension was cooled and the pH was adjusted to 5.8 with acetic acid. The brown solid was filtered and washed with water, 1:1 methanol water, methanol and finally ethyl acetate. Drying afforded 422 g of 6-(4-acetylaminophenyl)-1,2-dihydro-2-oxonicotinonitrile; mp >350°.
*All temperatures are shown in degrees Centigrade.

A suspension of 422 g (1.67 mol) of the above nitrile and 3650 ml of water containing 932 g of potassium hydroxide was heated at 105° for 40 hrs. The solution was cooled and acidified to pH 4.0 with 1360 ml of concentrated hydrochloric acid and 400 g of potassium hydroxide pellets were added with stirring. After filtration, the pH of the filtrate was adjusted to 4.5 with concentrated hydrochloric acid. The solid was filtered, suspended in 8 l of water and filtered. The solid was washed with methanol and finally ethyl acetate and dried at 60° to give 328 g, mp 314°–316° dec.

$E_1^1 = 944 \lambda 347$ nm pH 7

To a suspension of 20.14 g (87.5 mM) of 6-[4-aminophenyl]-1,2-dihydro-2-oxonicotinic acid in 600 ml of $CH_2Cl_2$ was added 36.9 ml (262.5 mM) of $Et_3N$ followed by 34 ml (262.5 mM) of $(CH_3)_3SiCl$. The mixture was stirred at room temperature for 45 min.

To a suspension of 22.95 g (175 mM) of N-acetyl-L-alanine in 440 ml of $CH_3CN$ was added 19.3 ml (175 mM) of N-methyl morpholine and the mixture cooled to $-20°$ C. Isobutyl chloroformate, 25.0 ml (192.5 mM), was added dropwise with stirring over 15 min and the mixture was stirred for 40 min at $-20°$ C. To this mixture was added the above prepared silylated pyridone acid, keeping the temperature below $-15°$ C. The mixture was stirred 4 hrs at 5° and overnight at room temperature. Isopropanol (100 ml) was added and the product filtered after 10 min and washed with $CH_2Cl_2$ followed by ether. Drying afforded 25.7 g of 6-[4-(N-acetyl-L-alanylamino)phenyl]-1,2-dihydro-2-oxonicotinic acid, mp 268° d.

$[\alpha]_D^{25} -72°$ (c0.65, pH 8.4)

To 10 ml of DMF was added 1.0 g of the above L-alanyl pyridone acid (2.91 mM) and 1.18 g of carbonyldiimidazole and the mixture was heated with stirring to 50° to 60° for 50 min. After cooling to room temperature, 7 ml of $CH_2Cl_2$ and 19 ml of ether were added and the imidazolide derivative was filtered, washed with $CH_2Cl_2$ and ether, and dried in vacuo, giving 1.09 g, mp 240°–241° C. dec.; $[\alpha]_D^{23} -16.3°$ (cl, DMSO).

To a suspension of 3.75 g (6.3 mM) of amoxicillin DMSO complex in 30 ml of DMF was added 2.0 g (5.1 mM) of the L-alanyl pyridone imidazolide and 0.8 ml (5.7 mM) of $Et_3N$. After stirring for 3.5 hrs at room temperature, the mixture was poured into ice water and acidified to pH 2.5 with HCl. The product was filtered, washed with ice water and resuspended in water. The pH was raised to 5.3 with NaOH and the clear solution lyophilized affording 3.0 g of the sodium salt of the final product; $[\alpha]_D^{23} -492°$ (cl, pH 7);

$$\left. \begin{array}{l} E_1^1 = 160 \lambda 269 \text{ nm} \\ = 424 \lambda 355 \text{ nm} \end{array} \right\} \text{pH 7.}$$

EXAMPLE 2

N-[6-[4-(N-Acetyl glycylamino)phenyl]-1,2-dihydro-2-oxonicotinyl]amoxicillin.

6-(4-aminophenyl)-2-oxo-1,2-dihydro-nicotinic acid, 5.75 g (25 mM) was suspended in 250 ml of dry methylene chloride, and 9.38 ml (75 mM) of $(CH_3)_3SiCl$ was added with stirring followed by dropwise addition of 10.5 ml (75 mM) of $Et_3N$. The mixture was stirred for 45 min and added to the solution below.

To a suspension of 3.51 g (30 mM) of N-acetyl glycine in 150 ml of acetonitrile, 3.3 ml (30 mM) of N-methylmorpholine was added. The stirred solution was cooled to $-20°$ C. and 2.5 ml (30 mM) of methyl chloroformate was added. After 20 min at this temperature, the silylated mixture above was added over a 30 min period keeping the temperature at $-20°$ C. The mixture was stirred 4 hrs at 0° C. and 18 hrs at room temperature. Acetone (20 ml) and water (80 ml) were added and after stirring for 0.5 hr, the mixture was filtered and washed with EtOH and ether. The dried 6-[4-(N-acetylglycylamino)phenyl]-1,2-dihydro-2-oxonicotinic acid weighed 5.88 g. A sample was purified by dissolving in aqueous base (pH 10) and acidifying to pH 2 with HCl, mp >300°;

$$\left. \begin{array}{l} E_1^1 = 341 \lambda 254 \text{ nm} \\ = 653 \lambda 331 \text{ nm} \end{array} \right\} \text{pH 7 buffer.}$$

To a suspension of 3.29 g (10 mM) of the N-acetylglycyl pyridone acid in 50 ml of DMSO was added 3.24 g (20 mM) of carbonyldiimidazole and the stirred solution was heated at 50°–60° C. for 30 min. After standing at room temperature for 4 hrs, 50 ml of acetonitrile and 100 ml of ether were added to precipitate the imidazolide derivative. Filtration and ether washing afforded 2.55 g of this compound.

To a suspension of 3.6 g (6 mM) of amoxicillin DMSO complex in 20 ml of DMSO was added 2.16 g (5.4 mM) of the acetyl glycyl pyridone imidazolide followed by 0.7 ml (5 mM) of $Et_3N$. After stirring at room temperature for 2.25 hrs the mixture was added to ice water and acidified to pH 2.5 with HCl. The precipitate was filtered and washed with water. The above named final product was suspended in water and the pH brought to 5.5 with NaOH, filtered and lyophilized giving 3.74 g of the sodium salt, $[\alpha]_D^{25} -466°$ (cl, pH 7);

$$\left. \begin{array}{l} E_1^1 = 153 \lambda 269 \text{ nm} \\ = 414 \lambda 358 \text{ nm} \end{array} \right\} \text{pH 7}$$

EXAMPLE 3

N-[6-[4-(N-Acetyl-DL-alanylamino)phenyl]-1,3-dihydro-2-oxonicotinyl]amoxicillin.

The Tri-Silyl derivative of 6-(4-aminophenyl)-1,2-dihydro-2-oxonicotinic acid was prepared as described in Example 1 from 23 g of the acid in 750 ml of $CH_2Cl_2$, 41.8 ml of $Et_3N$ and 42 ml of $(CH_3)_3SiCl$.

To a suspension of 26.2 g (200 mM) of N-acetyl-DL-alanine in 500 ml of $CH_3CN$ was added 22 ml (200 mM) of N-methylmorpholine and the mixture cooled to $-15°$ C. Methyl chloroformate, 17 ml (220 mM) was added dropwise and stirred for 30 min at $-15°$ C. The silylated mixture above was then added over 20 min at $-15°$ C. The mixture was stirred at $0°$ for 4 hrs and overnight at room temperature. Isopropanol (60 ml) was added and the product was filtered, washed with $CH_2Cl_2$, then ether and dried affording 33 g of 6-[4-(N-acetyl-DL-alanylamino)phenyl]-1,2-dihydro-2-oxonicotinic acid; mp $297°-298°$, $$E_1^1 = 327 \; \lambda \; 264 \text{ nm} \atop = 630 \; \lambda \; 331 \text{ nm} \Big\} \text{pH 7}$$

The imidazole derivative (10.8 g) was prepared according to the procedure in Example 1, using 10.2 g (30 mM) of the DL-alanine pyridone acid, 100 ml of DMF and 10.2 g (62 mM) of carbonyldiimidazole.

To a suspension of 3.36 g (5.5 mM) of amoxicillin DMSO complex in 25 ml of dimethylacetamide was added 1.95 g (5.0 mM) of the above imidazolide and the mixture stirred 2 hrs at room temperature. The solution was poured into ice water (150 ml) and the pH adjusted to 2.5 with HCl. The precipitate was filtered, washed with water and resuspended in ice water. The pH was raised to 6.8 with NaOH and lyophilized affording 2.84 g of the Na salt of the above named final product; $[\alpha]_D^{23}$ $-475°$ (cl, pH 7)

$$E_1^1 = 150 \; \lambda \; 268 \text{ nm} \atop = 405 \; \lambda \; 358 \text{ nm} \Big\} \text{pH 7}$$

EXAMPLE 4

N-[6-[4-(N-Dichloroacetyl-L-alanylamino)phenyl]-1,2-dihydro-2-oxonicotinyl]amoxicillin.

6-(4-Aminophenyl)-1,2-dihydro-2-oxonicotinic acid 5.76 g (25 mM) was silylated as in Example 1, and added to the following mixed anhydride solution.

To a solution of 8.35 g (37.5 mM) of N-benzyloxycarbonyl-L-alanine in 100 ml of $CH_3CN$ was added 4.1 ml (37.5 mM) of N-methylmorpholine. After cooling to $-20°$ C., the mixture was treated with 2.9 ml (37.5 mM) of methyl chloroformate and stirred for 30 min. The above silylated solution was added at $-10°$ C. and allowed to stir overnight at room temperature. The mixture was filtered and the filtrate evaporated to dryness in vacuo. Acetone (100 ml) and water (250 ml) were added and the product filtered, washed with acetone-water (1:3) and ether and dried, giving 7.7 g of 6-[4-(N-benzyloxycarbonyl-L-alanylamino)phenyl]-1,2-dihydro-2-oxonicotinic acid; $[\alpha]_D^{23}$ $-56.3°$ (cl, pH 7 MeOH-water);

$$E_1^1 = 257 \; \lambda \; 264 \text{ nm} \atop = 481 \; \lambda \; 330 \text{ nm} \Big\} \text{pH 7}$$

A suspension of 6.5 g (15 mM) of the benzyloxycarbonyl-L-alanyl pyridone acid in 60 ml of 30% HBr in acetic acid was stirred at room temperature for 40 min. The solution was filtered and the product isolated by adding 275 ml ethyl acetate and 100 ml of ether, filtering and washing with ethyl acetate and ether. The dried solid was suspended in water and the pH raised to 10.2 with concentrated $NH_4OH$. The filtered solution was evaporated in vacuo and the product isolated by filtration, washing with water, ethanol, and ether. The dried 6-[4-(L-alanylamino)phenyl]-1,2-dihydro-2-oxonicotinic acid weighed 4.0 g; $[\alpha]_D^{23}$ $+6.7°$ (cl, pH 10 MeOH-water);

$$E_1^1 = 300 \; \lambda \; 266 \text{ nm} \atop = 555 \; \lambda \; 330 \text{ nm} \Big\} \text{pH 7}$$

To a suspension of 4.5 g (15 mM) of the L-alanyl-pyridone acid in 40 ml of DMF was added 2.1 ml (15 mM) of $Et_3N$ and the solution cooled to $-78°$ C. The mixture was treated with 2.3 ml (15 mM) of dichloroacetic anhydride. After stirring for 30 min another 2.1 ml of $Et_3N$ and 1.2 g (5 mM) of anhydride were added and the solution brought to room temperature. The mixture on evaporation in vacuo and triturating with $CH_3CN$ was filtered, washed with $CH_3CN$ and ether and dried giving 5.65 g of 6-[4-(N-dichloroacetyl-L-alanylamino)phenyl]-1,2-dihydro-2-oxonicotinic acid; $[\alpha]_D^{23}$ $-21.1°$ (cl, 75% DMF-pyridine);

$$E_1^1 = 282 \; \lambda \; 266 \text{ nm} \atop = 516 \; \lambda \; 331 \text{ nm} \Big\} \text{pH 7}$$

To a suspension of 5.65 g of the above prepared dichloroacetyl pyridone acid (13.7 mM) in 45 ml of DMF was added 5.6 g of carbonyldiimidazole and warmed to $55°$ for 1 hr. After stirring 2 hrs at room temperature, the solvent was removed in vacuo and $CH_3CN$ (50 ml) and ether (200 ml) added to the residue. The solid was filtered, washed with $CH_3CN$, ether and dried affording 5.4 g of imidazolide.

To a solution of 2.24 g (3.7 mM) of amoxicillin DMSO complex in 20 ml of dimethylacetamide at $5°$ C. was added 1.5 g (3.25 mM) of imidazolide with stirring. After stirring 1.5 hrs at $5°$ and 1.5 hrs at room temperature, 1 ml (3.3 mM) of a 3.3 M solution of sodium 2-ethyl hexanoate in DMA was added. The mixture was added dropwise to 250 ml of ethyl acetate and 100 ml ether and the solid filtered and washed with ether. The dried solid was dissolved in 100 ml of cold water and the pH lowered to 2.6 with HCl. The solid was filtered, washed with water and resuspended in water. The pH was raised to 6.8 with NaOH and the solution lyophilized affording 2.3 g of the sodium salt of the above named product;

$[\alpha]_D^{23}$ $+139°$ (cl, 75% DMF/pyridine);

$$E_1^1 = 136 \; \lambda \; 268 \text{ nm}$$
$$= 357 \; \lambda \; 358 \text{ nm} \quad \Big\} \text{ pH 7}$$

EXAMPLE 5

N-[6-[4-(N-carbamido-L-alanylamino)phenyl]-1,2-dihydro-2-oxonicotinyl]amoxicillin.

To a suspension of 2.53 g (8.4 mM) of 6-[4-(L-alanylamino)phenyl]-1,2-dihydro-2-oxonicotinic acid (Example 4) in 100 ml of water was added 2.34 ml (16.8 mM) of $Et_3N$ followed by 3.4 g (42 mM) of potassium cyanate. After 3 hrs at room temperature the mixture was evaporated overnight under a hood. The precipitate which formed was dissolved with the addition of $Et_3N$ and 6.8 g (84 mM) of KCNO was added. After standing for 8 hrs at room temperature the mixture was allowed to evaporate overnight. The pH was lowered to 2.5 with HCl the product was filtered and washed with water, EtOH and ether. Drying afforded 2.6 g of N-carbamido derivative in the form of a monohydrate. The above described acid, 1.75 g (5.1 mM), 25 ml of DMF and 2.5 g (15.3 mM) of carbonyldiimidazole afforded 1.83 g of the corresponding imidazolide utilizing the earlier described procedure.

A mixture of 3.84 g (6.3 mM) of amoxicillin DMSO complex, 30 ml dimethylacetamide and 2.36 g (6.0 mM) of imidazolide was stirred for 3 hrs at room temperature. Next, 1.82 ml (6.0 mM) of 3.3 M solution of sodium 2-ethyl hexanoate in dimethylacetamide was added. After 30 min the product was precipitated by adding 200 ml of ethyl acetate, filtered, washed with ethyl acetate and ether and dried. The material was dissolved in 200 ml of ice water, acidified with HCl to pH 2.5, filtered, washed with water, suspended in water and the pH raised to 6.5 with NaOH and lyophilized to give 4.2 g of the sodium salt of the above named final product; $[\alpha]_D^{23}$ +181° (cl, 75% DMF- $$E_1^1 = 120 \; \lambda \; 267 \text{ nm}$$
$$= 370 \; \lambda \; 358 \text{ nm} \quad \Big\} \text{ pH 7}$$

EXAMPLE 6

N-[6-[4-(L-alanylamino)phenyl]-1,2-dihydro-2-oxonicotinyl]amoxicillin.

To a suspension of 4.25 g (14.1 mM) of 6-[4-(L-alanylamino)phenyl]-1,2-dihydro-2-oxonicotinic acid in 500 ml of $CH_3CN$ was added 6.97 g (60 mM) of methyl acetoacetate, 15 g of molecular sieves (4A-Linde, Union Carbide Corporation) and the mixture stirred at room temperature for 18 hrs. The reaction was refluxed for 24 hrs, filtered and evaporated to dryness in vacuo, affording 3.85 g of the N—$C(CH_3)$=$CHCO_2CH_3$ derivative.

A mixture of 3.85 g of above enamine (9.65 mM) in 30 ml DMF and 3.85 g (23.8 mM) of carbonyldiimidazole was reacted at 50°-60° C. for 1 hr and overnight at room temperature. The reaction mixture was evaporated in vacuo and to it was added 40 ml $CH_2Cl_2$, 100 ml ethyl acetate and 100 ml ether. After filtration, washing with ether and drying, 4.15 g of imidazolide was obtained.

To a solution of 1.8 g of enamine imidazolide (4.0 mM) in 20 ml of dimethylacetamide was added 2.56 g (4.2 mM) of amoxicillin DMSO complex at 5° C. The mixture was stirred for 2 hrs at 5° and poured into 125 ml of ice water. The solution was filtered through Celite (a filter aid) and the filtrate adjusted to pH 4.2 (from 6.8) with HCl. The product was filtered, washed with water and resuspended in 100 ml of ice water. The pH was adjusted to 5.5 with $NH_4OH$ solution and lyophilized to give 1.9 g of the sodium salt of the above named final product; $[\alpha]_D^{23}$ +170° (cl, 75% DMF-pyridine).

EXAMPLE 7

N-[6-[4-(N-Acetyl-γ-aminobutyrylamino)phenyl]-1,2-dihydro-2-oxonicotinyl]amoxicillin.

From 7.0 g (30.4 mM) of silylated 6-(4-aminophenyl)-1,2-dihydro-2-oxonicotinic acid, 8.83 g (60.8 mM) of N-acetyl- -aminobutyric acid, 6.3 g of methyl chloroformate, 8.5 ml of $Et_3N$ and 150 ml $CH_3CN$, were obtained 10.6 g of 6-[4-(N-acetyl-γ-aminobutyrylamino)phenyl]-1,2-dihydro-2-oxonicotinic acid.

The above prepared pyridone acid, 5.0 g (14 mM), carbonyldiimidazole, 8.0 g (49 mM) and DMF (50 ml) afforded 3.23 g of the imidazolide.

Amoxicillin DMSO complex, 5.25 g (7.8 mM), imidazolide, 2.95 g (7.2 mM), $Et_3N$, 10 ml (7.2 mM) and dimethylacetamide were reacted together for 4 hrs at room temperature giving 3.51 g of the sodium salt of the above named final product; $[\alpha]_D^{23}$ −245° (cl, pH 7).

EXAMPLE 8

N-[6-[4-(N-Acetyl-L-isoleucylamino)phenyl]-1,2-dihydro-2-oxonicotinyl]amoxicillin.

N-Acetyl-L-isoleucine, 12.0 g (69.2 mM), $CH_2Cl_2$ (184 ml), N-methylmorpholine, 7.62 ml (76.2 mM) and methyl chloroformate 5.89 ml (76.2 mM), were mixed followed by the addition of silylated 6-(4-aminophenyl)-1,2-dihydro-2-oxonicotinic acid, prepared from 7.97 g (34.6 mM) of acid in 240 ml of $CH_2Cl_2$, giving 9.41 g of 6-[4-(N-Acetyl-L-isoleucylamino)phenyl]-1,2-dihydro-2-oxonicotinic acid; $[\alpha]_D^{23}$ −42.8° (cl, pH 8.4).

The above prepared 5.0 g acid (12.9 mM), DMF, 30 ml and carbonylidiimidazole, 3.16 g (19.5 mM), yielded 5.28 g of the imidazolide; mp 152°-162° dec.

Amoxicillin DMSO complex, 8.73 g (12.6 mM), imidazolide, 5.0 g (11.48 mM), dimethylacetamide, 64 ml and $Et_3N$, 1.6 ml (11.4 mM), were reacted for 3.5 hrs at room temperature giving 6.54 g of the sodium salt of the above final product; $[\alpha]_D^{23}$ +381° (cl, pH 7).

EXAMPLE 9

N-[6-[4-(N-Acetyl-D-asparaginylamino)phenyl]-1,2-dihydro-2-oxonicotinyl]amoxicillin.

The silylated derivative of 6-(4-aminophenyl)-1,2-dihydro-2-oxonicotinic acid in 70 ml $CH_2Cl_2$ is added to a mixed anhydride prepared from N-Acetyl-D-asparagine 3.5 g (20 mM), N-methylmorpholine 2.2 ml (20 mM) in 50 ml DMA and isobutyl chloroformate, 2.9 ml (22 mM), by stirring at 5° C. for 1 hr and 3 hrs at room temperature. Next, 20 ml of isopropanol was added and evaporated. Water was added to the residue and the mixture filtered. After recrystallization from dimethylacetamide-methanol, 1.8 g of 6-[4-(N-acetyl-D-asparaginylamino)phenyl]-1,2-dihydro-2-oxonicitinic acid was obtained, mp 265°-266° C.

The above pyridone acid, 1.36 g (3.5 mM), DMF, 20 ml and carbonyldiimidazole, 1.4 g (8.6 mM), were mixed as described earlier to give 1.6 of the imidazolide, mp 190°-191° C.

Amoxicillin DMSO complex, 2.4 g (3.78 mM), dimethylacetamide 20 ml, imidazolide, 1.5 g (3.44 mM), and Et₃N, 0.5 ml (3.44 mM), were mixed at 5° for ½ hr and 4 hrs at room temperature, using the earlier described workup the reaction gave 1.90 g of the sodium salt of the above named final product; $[\alpha]_D^{23}$ −390° (cl, pH 7).

EXAMPLE 10

N-[6-[4-(N-Acetyl-DL-prolylamino)phenyl]-1,2-dihydro-2-oxonicotinyl]amoxicillin.

To a solution of 11.8 g (75 mM) of N-acetyl-DL-proline and 10.5 ml (75 mM) of triethylamine in 150 ml dichloromethane at −15° C., was added 9.75 ml (75 mM) of isobutyl chloroformate. The reaction mixture was stirred at about −10° C. for 30 min. To this reaction mixture was added a cold solution of 11.5 g (50 mM) of 6-(4-aminophenyl)-1,2-dihydro-2-oxonicotinic acid and 7.7 ml (55 mM) triethylamine in 200 ml of dimethylacetamide which was stirred while cooling in an ice bath for 3 hrs, then overnight at room temperature. The reaction mixture was evaporated to dryness, the residue was triturated with water, and the solid collected by filtration. The solid was washed with water and acetonitrile and dried to yield 13.2 g of 6-[4-(Nacetyl-DL-prolylamino)phenyl]-1,2-dihydro-2-oxonicotinic acid, mp 279°–281° dec.

A mixture of 7.586 g (20 mM) of 6-[4-(N-acetyl-DL-prolylamino)phenyl]-1,2-dihydro-2-oxonicotinic acid and 6.48 g (40 mM) of carbonyldiimidazole in 150 ml of THF was stirred at 52°–56° for 1 hr and overnight at room temperature. The solid product was filtered and washed with THF and ether. After drying, 7.30 g of the imidazolide was obtained.

A reaction mixture containing 4.20 g (10.0 mM) of imidazolide, 6.62 g (10.0 mM) amoxicillin DMSO complex, 1.4 ml (10 mM) triethylamine and 75 ml DMF was stirred for 1.5 hours with ice bath cooling and 2 hours at room temperture. The reaction solution was poured into 500 ml of ice and water and acidified with 1 N HCl to pH 2.8. The solid was collected by filtration and washed with cold water. The solid was suspended in 250 ml water and cooled with an ice bath. To this suspension 1 N NaOH was added dropwise until a solution of pH 6.5 was obtained. The solution was filtered and freeze dried to obtain 6.1 g of the sodium salt of the above named product; $[\alpha]_D^{23}$ +162° (c 1.025, 75% DMF/pyridine).

EXAMPLE 11

N-[6-[4-(N-Acetyl-L-prolylamino)phenyl]-1,2-dihydro-2-oxonicotinyl]amoxicillin.

To a suspension of 5.75 g (25 mM) 6-(4-aminophenyl)-1,2-dihydro-2-oxonicotinic acid and 175 ml of dichloromethane, 10.5 ml (75 mM) triethylamine and 9.5 ml (75 mM) chlorotrimethylsilane were added and stirred at room temperature for 1 hour. To a solution of 7.86 g (50 mM) of N-Acetyl-L-proline in 100 ml of dichloromethane at −10° C., 5.5 ml (50 mM) of N-methylmorpholine and 6.5 ml (50 mM) of isobutyl chloroformate were added and stirred at −10° C. for ½ hour. To this cold mixed anhydride mixture was added the silylated 6-(4-aminophenyl)-1,2-dihydro-2-oxonicotinic acid and the resulting mixture was stirred for 3 hrs in an ice bath and overnight at room temperature. Next, 25 ml of isopropanol was added to the reaction mixture and stirred. The reaction mixture was evaporated and the residue was triturated with ice and water. The solid was collected by filtration and washed with water, isopropanol and ether to yield 4.82 g of 6-[4-(N-acetyl-L-prolylamino)phenyl]-1,2-dihydro-2-oxonicotinic acid, mp 288°–290° dec. From the filtrate an additional 3.94 g of product was obtained.

A solution of 4.30 g (11.6 mM) of 6-[4-(N-acetyl-L-propyl)aminophenyl]-1,2-dihydro-2-oxonicotinic acid, 3.77 g (23.2 mM) of carbonyldiimidazole and 50 ml of DMF were heated at 50°–58° C. for 1 hour and then stirred at room temperature overnight. To the reaction mixture, 50 ml of THF and 200 ml of ether was added. The precipitated solid was collected and washed with ether to yield 3.08 g of imidazolide.

Next, 3.04 g (7.25 mM) of imidazolide, 4.57 g (7.75 mM) of amoxicillin DMSO complex, 50 ml dimethylacetamide and 1.01 ml (7.25 mM) triethylamine are stirred together and worked up to give the above named final product in the same way as that used to prepare the compound of Example 10. The yield of the sodium salt of the final product $[\alpha]_D^{23}$ −468° (c 1.00, pH 7) was 5.0 g.

EXAMPLE 12

N-[6-[4-(N-Acetyl-L-glutaminylamino)phenyl]-1,2-dihydro-2-oxonicotinyl]amoxicillin.

The tri-silyl derivative of 6-(4-aminophenyl)-1,2-dihydro-2-oxonicotinic acid was prepared as described in Example 1 from 57.5 g (0.25 mol) of the acid, 105 ml (0.75 mol) of triethylamine, and 95 ml (0.75 mol) of chlorotrimethylsilane in 1.9 L of dichloromethane.

To a solution of 105 g (0.37 mol) of N-benzyloxycarbonyl-L-glutamine in 1.12 L of dry dimethylacetamide cooled to −10° was added 41 ml (0.37 mol) of N-methylmorpholine and 28.6 ml (0.37 mol) of methyl chloroformate. After stirring for 30 min at −10° to −15° the above silylated mixture was added while maintaining the reaction temperature below 5°. The mixture was stirred at 5° for 4 hrs and at room temperature overnight. The mixture was concentrated on a rotary evaporated to remove the dichloromethane and with a vacuum pump to remove the dimethylacetamide. Ice water was added to the residue and the solid filtered and washed with water, methanol, and ether and dried to give 106 g of 6-[4-(N-benzyloxycarbonyl-L-glutaminylamino)phenyl]-1,2-dihydro-2-oxonicotinic acid; $[\alpha]_D^{23}$ +17.3° (cl, DMSO).

To 217 g of freshly prepared 31% HBr/acetic acid was added 46.8 g of the above N-benzyloxycarbonyl compound and the reaction mixture was stirred at room temperature for 2 hrs. To the reaction mixture was added 200 ml of ethyl acetate and stirring continued for 40 min. The salt was collected by filtration and washed with ethyl acetate and ether. The solid was suspended in 300 ml of water and 100 ml of concentrated ammonium hydroxide was added. After stirring for about 30 min the solution was clarified by filtration and the filtrate concentrated to about 100 ml on a rotary evaporator. The solid was filtered, washed with water, methanol, and ether to give 30.0 g of 6-[4-(L-glutaminylamino)-phenyl]-1,2-dihydro-2-oxonicotinic acid; $[\alpha]_D^{23}$ +37° (cl, DMSO).

A solution of 30.6 g (0.083 mol) of 6-[4-(L-glutaminylamino)phenyl-1,2-dihydro-2-oxonicotinic acid 400 ml of dimethylformamide, 56 ml (0.4 mol) of triethylamine, and 19 ml (0.2 mol) of acetic anhydride was stirred at room temperature for 3 hours. The reaction solution was evaporated to dryness with a rotary evaporator and the residue was treated with ice and water. The solid was filtered, washed with water, methanol, ether and dried to give 27.6 g of 6-[4-(N-acetyl-L-glutaminylamino)phenyl]-1,2-dihydro-2-oxo-nicotinic acid; $[\alpha]_D^{23}$ +19° (cl, DMSO).

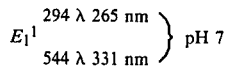
} pH 7

Alternate method for the preparation of 6-[4-(N-acetyl-L-glutaminylamino)phenyl]-1,2-dihydro-2-oxonicotinic acid.

A mixture of 309 g (1.64 mol) of acetyl-L-glutamine, 22 g (1.12 mol) of bis(trimethylsilyl)-acetamide (BSA) and 5194 ml of tetrahydrofuran was stirred at room temperature for 4 days. Insoluble material was filtered off and 59.4 g (0.81 mol) of dry dimethylformamide was added to the filtrate followed by 20 ml of tetrahydrofuran. The temperature lowered to −35° C. and a solution of 96.7 g (0.82 mol) of thionyl chloride in 522 ml of dichloromethane, kept at −17° C., was added during a 40 min period while maintaining the reaction temperature at −34.2 to −36° C. for 1 hour.

A mixture of 145.5 g (0.63 mol) of 6-(4-aminophenyl)-1,2-dihydro-2-oxonicotinic acid, 217 g (1.07 mol) of BSA, 654 ml of tetrahydrofuran and 1668 ml of dichloromethane was stirred at room temperature for 3 days, filtered and washed with 920 ml of dichloromethane containing 0.01% of BSA. The filtrate, kept at −48° to −54° C., was added to the above acid chloride during a 1.5 hour period while maintaining the reaction temperature at −35° C. The reaction mixture was stirred at −35° to −36° C. for 1 hour and at −33° C. for 14 hours. The reaction mixture was concentrated under reduced pressure at a bath temperature of 34° to 40° C. to a yellow slurry and 3.1 L of ice cold 95% ethanol was added. The mixture was stirred for 30 min and then stored overnight at −35° C. The suspension was centrifuged and the supernatant was decanted. The residual solid was washed with 1.2 L of 95% ethanol and centrifuged. The process was repeated and the solid obtained was stored at −30°. This product and that from a duplicate run are combined and treated with 4 L of water in a homogenizer for 30 min and 28 L of water was added. Stirring was continued for 1.5 hours and the solid was collected by centrifugation and washed with 2 L of water. The solid was stirred in 4 L of water for 30 min and centrifuged. After decantation, the residual solid was washed successively in a similar manner with 3 L of water and 2 portions each of 1.75 L of acetonitrile. The solid was washed with 3 L of ether, filtered and dried to give 439.4 g of 6-[4-(N-acetyl-L-glutaminylamino)-phenyl]-1,2-dihydro2-oxonicotinic acid; $[\alpha]_D^{23}$ +18.1° (cl, DMSO).

A mixture of 28.0 g (0.07 mol) of the above pyridone acid, 17.0 g (0.15 mol) of carbonyldiimidazole, and 200 ml of dimethylformamide was heated with stirring at 50°-55° for 1 hr. The resulting solution was stirred at room temperature overnight and diluted with 500 ml of acetonitrile. The mixture was stirred for 30 min and the solid filtered and washed with acetonitrile and ether and dried to give 26.4 g of the imidazolide; $[\alpha]_D^{23}$ +18.3° (cl, DMSO).

A mixture of 12.4 g (27.5 mM) of imidazolide, 12.71 g (30.3 mM) of amoxicillin trihydrate and 190 ml of di-methylacetamide was stirred at 0°-5° C. for 4 hrs. The reaction solution was added to 1.9 L of water at 19°-20° over a 6 min period. The pH was adjusted to 2.5 with 12% hydrochloric acid and the precipitated solid was stirred for 5 min and allowed to stand for 10 min. The solid was isolated by centrifugation and washed with 2 L of water at 20° C. and resuspended in cold water. The pH was adjusted to 6.0 with 1 N sodium hydroxide. The solution was clarified by filtration and lyophilized to give 17.74 g of the above named final product as the sodium salt; $[\alpha]_D^{23}$ −414° (cl, pH 7).

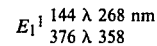

EXAMPLE 13

N-[6-[4-(N-Trifluoroacetylglycylamino)phenyl]-1,2-dihydro-2-oxonicotinyl]amoxicillin.

To a suspension of 8.6 g (50 mM) of trifluoroacetylglycine in 200 ml $CH_2Cl_2$, was added in portions 8.1 g (50 mM) of carbonyldiimidazole. The reaction mixture was stirred for 3 hrs at room temperature and then was added to a preformed silylated solution (formed by stirring 5.8 g (2.5 mM) of aminophenylpyridone acid; 9.6 ml (75 mM) $Me_3SiCl$; 10.5 ml (75 mM) $Et_3N$ in 250 ml $CH_2Cl_2$ for 1 hr at 0° C. After the addition, the reaction mixture was allowed to stir at room temperature for 12 hrs. The resulting solution was evaporated in vacuo, the residue was triturated in water, solids filtered, washed with ethyl acetate, dried to give 7.8 g of 6-[4-(N-trifluoroacetylglycylamino)phenyl-1,2-dihydro-2-oxonicotinic acid.

A suspension of 7.6 g (20 mM) of the above formed pyridone acid, 4.80 g (30 mM) of carbonyldiimidazole in 50 ml dimethylacetamide was stirred at 60° C. for ½ hr then at room temperature for 3 hrs. The resulting clear solution was precipitated by adding 250 ml of ether. The solids were filtered, washed with ether and dried to yield 8.6 g of the corresponding imidazolide.

A cold mixture of 6.9 g (11 mM) of amoxicillin DMSO complex, 4.33 g (10 mM) of the imidazolide and 1.4 ml (10 mM) $Et_3N$ in 40 ml dimethylacetamide was let stand at room temperature for 3 hrs. To the resulting solution was added sodium 2-ethylhexanoate, 3.45 ml (10 mM), and the product was precipitated by pouring into 600 ml of ethyl acetate with good stirring. The solids were filtered, dried and dissolved in ice water. The solution was acidified to pH 2.5 with 1 N HCl and the solids filtered, suspended in ice water, filtered and resuspended in water, adjusted to pH 6.5 with 1 N NaOH, filtered and the filtrate was freeze dried. The dried solids were again dissolved in water, filtered and the filtrate was acidified to pH 2.5 with 1 N HCl. The solids were filtered off, suspended in water, filtered and resuspended in water, adjusted to pH 6.5, and filtered. The filtrate was freeze dried to give 2.5 g of the above named final product as the sodium salt; $[\alpha]_D^{23}$ +509° (c 1.00, pH 7).

EXAMPLE 14

N-[6-[4-(N-Trifluoroacetyl-alpha-aminoisobutyrylamino)phenyl]-1,2-dihydro-2-oxonicotinyl]amoxicillin.

A solution of pivaloyl chloride, 1.3 ml (10 mM) in 10 ml $CH_2Cl_2$, was added to a suspension of 1.99 g (10 mM) of the N-trifluoroacetyl-alpha-aminoisobutyric acid [Tetrahedron 11, 39 (1960)] and 1.9 ml (13 mM) Et$_3$N in 15 ml CH$_2$Cl$_2$ at −10° C. The mixture was stirred at −5° C. for 1 hr, the resulting mixture was then added to a preformed silylated aminophenylpyridone solution (1.15 g; 5 mM of aminophenylpyridone, 1.5 ml bis-(trimethylsilyl)acetamide in 10 ml DMF) at −5° C. The mixture was stirred at 0° C. for ½ hr, at room temperature for 6 hrs. The reaction mixture was filtered, the filtrate was evaporated in vacuo and the residue triturated in water, solids filtered, dried to give 1.6 g of 6-[4-(N-trifluoroacetyl-alpha-aminoisobutyrylamino)-phenyl]-1,2-dihydro-2-oxonicotinic acid.

Carbonyldiimidazole, 1.0 g (6 mM), was added to a mixture of 1.6 g (4 mM) of the above prepared pyridone acid in 10 ml dimethylacetamide at 50° C. The immediate solution was allowed to stand at room temperature for 3 hrs, 40 ml of THF was added and stored in a refrigerator for 10 hrs. Scratching on the side of the flask afforded crystalline material which was filtered, dried to yield 1.05 g of the corresponding imidazolide.

A solution of 1.7 g (2.5 mM) of amoxicillin DMSO complex and 1.05 g (2.2 mM) of the imidazolide in 10 ml DMA was allowed to stir at 0° C. for 2 hrs, then stand at room temperature for 1 hr, and the resulting solution was poured into 100 ml ice water. The clear solution was acidified to pH 2.5 with 1 N HCl. The product was filtered, suspended in 100 ml ice water, filtered and resuspended in 50 ml ice water, adjusted to pH 6.0 with 1 N NaOH. This solution was freeze dried to give 1.3 g of the above named final product as the sodium salt;

EXAMPLE 15

N-[6-[4-(N-Acetyl-alpha-aminoisobutyrylamino)-phenyl]-1,2-dihydro-2-oxonicotinyl]amoxicillin.

Methyl chloroformate, 1.7 ml (20 mM), was added to a solution of 2.9 g (20 mM) of alpha-acetamidoisobutyic acid, 2.2 ml (20 mM) of N-methylmorpholine in 50 ml CH$_3$CN at −15° C. The mixture was stirred at −20° C. to −10° C. for ½ hr and to it was added in a dropwise manner preformed silylated pyridone solution (by stirring a mixture of 2.3 g (10 mM) of the 6-(4-aminophenyl)-1,2-dihydro-2-oxonicotinic acid, 3.84 ml (30 mM) of Me$_3$SiCl, 4.2 ml (30 mM) of Et$_3$N in 100 ml CH$_2$Cl$_2$ for 40 min) at −10° C. After the addition, the mixture was allowed to stir at 0° C. for 2 hrs and at room temperature for 12 hrs. To the resulting suspension was added 10 ml of isopropanol, stirred for 10 min, and the solids filtered, washed with MeOH, ether, dried to give 2.5 g of 6-[4-(N-acetyl-alpha-amino-isobutyrylamino)phenyl]-1,2-dihydro-2-oxonicotinic acid.

The above prepared acylated aminophenylpyridone acid 3.2 g (9 mM) was converted to the corresponding imidazolide with 3.24 g (20 mM) of carbonyldiimidazole by the procedure given in Example 14, yielding 2.08 g of product.

The imidazolide, 2.08 g (5.1 mM), was reacted with amoxicillin DMSO complex, 3.8 g (6 mM), in 20 ml dimethylacetamide using the procedure of Example 14, giving 3.3 g of the sodium salt of the above named final product; $[\alpha]_D^{23}$ +213° (cl, 75%, DMF/pyridine).

EXAMPLE 16

N-[6-[4-(N-Acetyl-L-cysteiylamino)phenyl]-1,2-dihydro-2-oxonicotinyl]amoxicillin.

A silylated derivative of 6-(4-aminophenyl)-1,2-dihydro-2-oxonicotinic acid, 9.0 g (39 mM) in 250 ml CH$_2$Cl$_2$ and 25 g (118 mM) of N-acetyl-L-cysteic acid $[[\alpha]_D^{23}$ −26.2° (Cl, 1 N HCl)], 11.9 g (118 mM) N-methylmorpholine and 11.2 g of methyl chloroformate (118 mM) in 300 ml of dimethylacetamide acetonitrile (1:1) were mixed together to give 8.2 g of 6-[4-(N-acetyl-L-cysteiylamino)phenyl]-1,2-dihydro-2-dihydro-2-oxonicotinic acid;

$$E_1^1 = \left.\begin{array}{l} 339 \lambda\ 265\ nm \\ 707 \lambda\ 334\ nm \end{array}\right\} pH\ 7$$

Mixing 5.5 g (12.9 mM) of the above acid, 125 ml of DMSO and 3.5 g (21.6 mM) of carbonyldiimidazole afforded 4.5 g of the corresponding imidazolide.

Mixing 5.0 g of amoxicillin DMSO complex (8.2 mM) in 50 ml DMSO and 3.9 g (8.2 mM) of imidazolide gave 7.8 g of the above named final product. The product was dissolved in water, the pH adjusted to 7.5 and centrifuged. Supernatant on lyophilization gave 6.1 g of pure product as the sodium salt; $[\alpha]_D^{23}$ −380° (cl, pH 7);

$$E_1^1 = 325\ \lambda\ 362\ nm\ \}\ pH\ 7$$

EXAMPLE 17

N-[6-[4-(N-Acetyl-L-serylamino)phenyl]-1,2-dihydro-2-oxonicotinyl]amoxicillin.

From 7.0 g (30 mM) of silylated 6-(4-aminophenyl)-1,2-dihydro-2-oxonicotinic acid, 17.4 g (91 mM) of diacetyl-L-serine, 9.1 g (91 mM) of N-methylmorpholine and 8.6 g (91 mM) of methyl chloroformate in 100 ml of dimethylacetamide and 100 ml of CH$_3$CN, gave 7.5 g of 6-[4-(N-acetyl-L-serylamino)phenyl]-1,2-dihydro-2-oxonicotinic acid; $[\alpha]_D^{23}$ −8.7° (cl, DMF);

$$E_1^1 \begin{array}{l} = 264\ \lambda\ 265\ nm \\ = 488\ \lambda\ 330\ nm \end{array} \Big\} pH\ 7$$

Next, 5.0 g (15.7 mM) of the above acid, 50 ml DMA, 1.6 g (14 mM) of N-hydroxysuccinimide and 2.9 g of dicyclohexylcarbodiimide are allowed to stand at room temperature for 24 hrs. After filtration, the filtrate was evaporated in vacuo. Addition of isopropanol to the residue gave 5.0 g of the corresponding activated ester.

From 5.0 g (8.2 mM) of amoxicillin DMSO complex, 3.4 g (8.2 mM) of activated ester and 50 ml DMSO, 2.76 g of the above named final product was obtained as the sodium salt; $[\alpha]_D^{23}$ −111° (cl, pH 7);

$$E_1^1 \begin{array}{l} = 172\ \lambda\ 267\ nm \\ = 350\ \lambda\ 355\ nm \end{array} \Big\} pH\ 7$$

EXAMPLE 18

N-[6-[4-(N-Acetyl-L-hydroxyprolylamino)phenyl-1,2-dihydro-2-oxonicotinyl)amoxicillin.

A suspension of 172.5 g (0.75 mol) of 6-(4-aminophenyl)-1,2-dihydro-2-oxonicotinic acid, 312 ml (2.23 mol) of triethylamine, and 11.8 L of dichloromethane was stirred at 10° and 290 ml (2.28 mol) of chlorotrimethylsilane is slowly added. The resulting mixture was stirred overnight at room temperature. A mixture of 273 g (1.58 mol) of N-acetyl-4-hydroxy-L-proline and 3.5 L of dichloromethane was stirred at −15° and 177.5 ml (1.61 mol) of N-methylmorpholine was added during a 20 min period followed by 250 ml of dichloromethane. The mixture was stirred at −13° for 15 min and 125.5 ml (1.62 mol) of methyl chloroformate was added over a 25 min period at −14° followed by 150 ml of dichloromethane. The mixture was stirred at −15° for 40 min and the above silylated nicotinic acid was added over a period of 60 min at −17° followed by 500 ml of dichloromethane. The mixture was stirred for 1 hr and 40 min as the temperature rose to 1°. The mixture was stirred overnight with ice bath cooling as the temperature rose to 16° and 135 ml of glacial acetic acid was added followed by 135 ml of isopropanol. The reaction mixture was concentrated to 4 L under reduced pressure and the solid filtered, washed with dichloromethane and dried to give 245 g of 6-[4-(N-acetyl-4-hydroxy-L-prolylamino)phenyl]-1,2-dihydro-2-oxonicotinic acid.

A mixture of 50.0 g (0.31 mol) of the above pyridone acid 72.2 ml (0.754 mol) of 2-methoxypropene, and 190 ml of N,N-dimethylacetamide was stirred at room temperature overnight. The solution was clarified by filtration and the filtrate was diluted with 400 ml of acetonitrile and stirred at room temperature for 1.5 hr. The solid was filtered, washed with acetonitrile and ether and dried briefly under vacuum to give 46 g of product. The unstable product was converted to the imidazolide below.

A mixture of the above product (46 g), 42.2 g (0.26 mol) of carbonyldiimidazole, 6 ml of N,N-dimethylacetamide, and 650 ml of acetonitrile is stirred at 50° for 40 min and cooled to 0°–5°. The solid was filtered, washed with acetonitrile and ether and dried to give 45.0 g of 6-[4-[N-acetyl-4-(1-methoxy-1-methylethoxy)-L-prolylamino]phenyl]-1,2-dihydro-2-oxonicotinic acid imidazolide; $[\alpha]_D^{23}$ +15° (cl, DMSO).

To a stirred solution of 6.11 g (12 m mol) of the above imidazolide in 38 ml of dimethylacetamide at 5° was added 9.84 g (14.6 m mol) of amoxicillin DMSO Complex. The reaction mixture was stirred at 5° for 5 hrs and then poured into 200 ml of ice water. The pH of the solution was adjusted to 6.8 with dilute acetic acid and extracted 3 times with cold ethyl acetate. The pH of the aqueous layer was adjusted to 2.6 with hydrochloric acid during 90 min while the mixture was being stirred in an ice bath. The solid was filtered, washed with cold water and suspended in 150 ml of water. The pH was brought to 6.0 with 1 N sodium hydroxide and the solution was clarified by filtration. The filtrate was lyophilized to give 8.22 g of the sodium salt of the above named final product; $[\alpha]_D^{23}$ −460° (c 0.95, pH 7).

$$E_1^1 \left. \begin{array}{l} 146 \lambda \, 270nm \\ 384 \lambda \, 358nm \end{array} \right\} pH\ 7$$

EXAMPLE 19

N-[6-[4-(N-Formyl-L-alanylamino)phenyl]-1,2-dihydro-2-oxonicotinyl]amoxicillin.

A suspension of 1.0 g (3.3 mM) of 6-[4-(L-alanylamino)phenyl]-1,2-dihydro-2-oxonicotinic acid, Example 4, and 6 ml of DMF was stirred at 5° C. Addition of 1.5 ml of Et₃N gave a clear solution. A 3 ml portion of acetic-formic anhydride [Fieser & Fieser "Reagents for Organic Synthesis," Vol. 1, p. 4, 1967] was added and the mixture stirred at 5° C. for 30 minutes. Addition of 0.6 ml Et₃N gave a clear solution which was stirred at 5° C. for 40 minutes. Another 2 ml of the anhydride was added and the mixture stirred at room temperature for 2 hours. The reaction mixture was poured into water and the pH adjusted to 8 with Et₃N. The pH of the solution was lowered to 3.6 with aqueous HCl and the resulting solids filtered, washed with water and dried, giving 0.86 g of 6-[4-(N-formyl-L-alanylamino)phenyl]-1,2-dihydro-2-oxonicotinic acid; $[\alpha]_D^{23}$ −50° (Cl, 75% DMF-pyridine;

$$E_1^1 \left. \begin{array}{l} = 620 \lambda \, 331\ nm \\ = 332 \lambda \, 265\ nm \end{array} \right\} pH\ 7$$

A mixture of 3.64 g (8 mM) of the above described acid, 13 ml of DMF, and 2.6 g (16 mM) of carbonyldiimidazole was heated at 60° C. with stirring for 1 hour. The reaction mixture was cooled to room temperature and 25 ml of acetonitrile and 25 ml of ether was added. The solids were filtered and dried affording 2.31 g of the corresponding imidazolide.

According to the procedure of Example 5, a mixture of 3.9 g (6.4 mM) of amoxicillin DMSO complex, 2.31 g (6.1 mM) of the above imidazolide, and 20 mil of DMF was reacted at room temperature for 2¼ hours. Isolation and lyophilization of the aqueous solution at pH 5 gave 4.08 g of the sodium salt of the above named final product; $[\alpha]_D^{23}$ −314° (cl, pH 7.0);

$$E_1^1 \left. \begin{array}{l} = 160 \lambda \, 268\ nm \\ 415 \lambda \, 358\ nm \end{array} \right\} pH\ 7$$

EXAMPLE 20

N-[6-[4-(N-Acetyl-L-alanyl-L-alanylamino)phenyl]-1,2-dihydro-2-oxonicotinyl]amoxicillin.

A mixture of 4.50 g (15 mM) of 6-[4-(L-alanylamino)-phenyl]-1,2-dihydro-2-oxonicotinic acid, Example 4, 1.97 g (15 mM) N-acetyl-L-alanine, 2.02 g (15 mM) 1-hydroxybenzotriazole, and 150 ml of DMF was stirred at room temperature and 3.09 g (15 mM) of dicyclohexylcarbodiimide was added. After 19 hours the reaction mixture was filtered and the filtrate evaporated to dryness. Water was added and the solids filtered, washed with hot ethyl acetate and ether, and dried, giving 5.01 g of 6-[4-(N-acetyl-L-alanyl-L-alanylamino)phenyl]-1,2-dihydro-2-oxonicotinic acid.

A suspension of 4.90 g (11.85 mM) of the above described acid, 3.84 g (23.7 mM) of carbonyldiimidazole, and 60 ml of DMF was stirred at 47° to 53° for 30 minutes and at room temperature overnight. Tetrahydrofuran (60 ml) and ether (120 ml) were added and the solids filtered, washed with THF and ether and dried to give 3.53 g of the corresponding imidazolide.

A suspension of 4.81 g (7.62 mM) of amoxicillin DMSO complex, 3.53 g (7.62 mM) of the above imidazolide, 1.07 ml (7.62 mM) Et₃N, and 50 ml of dimethylacetamide was stirred at ice bath temperature for 10 minutes and at room temperature for four hours. The solution was poured into 350 ml of ice water and the pH adjusted to 1.5 with 1 N HCl. The precipitated solids were filtered and suspended in water. The pH was brought to 6.5 with 1 N NaOH and the mixture filtered and the filtrate lyophilized to give 4.32 g of crude product. The solids were purified by treating with 100 ml of methanol. Insolubles were filtered and 150 ml each of THF and ether added to the filtrate. The resulting solids were filtered, washed with ether, dissolved in 100 ml of water and lyophilized to afford 1.72 g of the sodium salt of the above named final product; $[\alpha]_D^{23}$ −15.3° (c1, pH 7).

EXAMPLE 21

N-[6-[4-(L-Pyroglutamylamino)phenyl]-1,2-dihydro-2-oxonicotinyl]amoxicillin.

The silylated derivative of 6-(4-aminophenyl)-1,3-dihydro-2-oxonicotinic acid was prepared by the method of Example 1 from 23 g (0.1 mol) of the acid, 40 ml (0.32 mol) of trimethylchlorosilane, 28 ml (0.3 mol) of Et$_3$N, and 700 ml of CH$_2$Cl$_2$, and cooled to 5° C. with an ice bath. A solution of 22.1 g (0.15 mol) L-pyroglutamic acid chloride [West German Pat. No. 2,456,634] and 100 ml of CH$_2$Cl$_2$ was slowly added to the above silylated pyridone acid solution. The reaction was stirred at 5° C. for 30 minutes and at room temperature for 3 days. The CH$_2$Cl$_2$ was evaporated and water and methanol was added. The brown solids were filtered and washed with hot methanol and dried to give 27 g of 6-[4-(L-pyroglutamylamino)phenyl]-1,2-dihydro-2-oxonicotinic acid; $[\alpha]_D^{23}$ +12.1° (c1, pH 8).

A mixture of 3.41 g (10 mM) of the above described acid, 3.24 g (20 mM) of carbonyldiimidazole, and 50 ml of DMF was stirred at 52° to 55° for 45 minutes and then at room temperature overnight. Acetonitrile (200 ml) was added and the mixture allowed to stand for 2 hours. The solids were filtered, washed with acetonitrile and ether and dried to give 2.56 g of the corresponding imidazolide.

A solution of 4.49 g (6.5 mM) of amoxicillin DMSO complex, 2.55 g (6.5 mM) of the above imidazolide, 0.91 ml (6.5 mM) of Et$_3$N, and 50 ml of dimethylacetamide was stirred at 5° C. for 10 minutes and then at room temperature for 3.5 hours. The solution was poured into 300 ml of ice water and the pH adjusted to 2.0 with 1 N HCl. The solids were filtered, suspended in water and refiltered. The solids were suspended in 100 ml of water with cooling and the pH adjusted to 6.2 with 1 N NaOH, filtered, and lyophilized giving 4.0 g of the sodium salt of the above named final product; $[\alpha]_D^{23}$ −201° (c1, pH 7).

EXAMPLE 22

N-[6-[4-(N,N′-Diacetyl-DL-lysylamino)phenyl]-1,2-dihydro-2-oxonicotinyl]amoxicillin.

A solution of 21.9 g (0.15 mol) of L-lysine, 20 ml of pyridine, and 20 ml of water was stirred at room temperature and 40 ml (0.41 mol) of acetic anhydride was added during a 2 hour period. The resulting solution was stirred overnight at room temperature. Another 20 ml of acetic anhydride were added and the solution heated at 40° C. for 3 hours to complete the reaction and the reaction mixture was evaporated to a syrup. The crude product was purified by passing a water solution over a column of 80 g of Amerlite IR-120 resin and eluting with 1500 ml of water. The water was evaporated and the residue crystallized from acetone to afford 15.7 g of N,N′-diacetyl-DL-lysine, mp 138°–139° C. A second crop of 10.3 g, mp 138°–139° C. was obtained from acetoneacetonitrile.

The silylated derivative of 6-(4-aminophenyl)-1,2-dihydro-2-oxonicotinic acid was prepared by the method of Example 1 from 2.3 g (10 mM) of the acid, 3.35 g (33 mM) of trimethylchlorosilane, 3.1 g (31 mM) Et$_3$N, and 150 ml of CH$_2$Cl$_2$.

A stirred solution of 4.6 g (20 mM) of N,N′-diacetyl-DL-lysine, 2.02 g (20 mM) of N-methylmorpholine, and 60 ml of DMF was cooled to −15° and 2.72 g (20 mM) of isobutylchloroformate was added during a 10 min period while maintaining the temperature at −10° to 15° C. Stirring was continued for 25 minutes at ca. −12° C. and the above silylated mixture was added at −12° to −14° C. over 15 minutes. The resulting mixture was stirred at −10° C. for 10 minutes and then overnight while warming from 5° C. to room temperature as the ice bath melted. Isopropanol (15 ml) was added and the reaction mixture stirred for 2 hrs at 25° C. The solids were filtered, washed with isopropanol and water and air dried to afford 3.6 g of 6-[4-(N,N′-diacetyl-DL-lysylamino)phenyl]-1,2-dihydro-2-oxonicotinic acid, mp 276°–277° dec. Recrystallization from DMF-acetonitrile gave compound with mp 277°–278° dec., $[\alpha]_D^{23}$ +1.6° (c1, DMSO), $[\alpha]_D^{23}$ −1.2° (c1, pH 8.4).

A mixture of 2.21 g (5 mM) of the above acid and 60 ml of DMF was heated to 65° C. and filtered to remove insolubles. The filtrate was treated with 1.62 g (10 mM) of carbonyldiimidazole and heated at 55° C. for 1 hr and then kept at room temperature overnight. Acetonitrile (230 ml) was added over a 1 hour period with stirring at room temperature and stirring continued for another 3 hours. The solids were filtered and washed with acetonitrile to give 1.9 g of the corresponding imidazolide, mp 220°–221° C., $[\alpha]_D^{23}$ −1.4° C. (c1, DMSO).

A mixture of 2.9 g (3.95 mM) of amoxicillin DMSO complex, 1.9 g (3.86 mM) of the above imidazolide, and 40 ml of dimethylacetamide was stirred at room temperature for 4 hours. Triethylamine 0.39 g (3.86 mM) was added and stirring continued for 30 minutes. The reaction mixture was poured into 150 ml of ice water and the pH adjusted to 2.0 with 0.1 N NCl. The solids were filtered, suspended in cold water and filtered. The solids were resuspended in cold water, and were brought into solution by adjusting the pH to 6.5 with 0.1 N NaOH. Lyophilization gave 2.2 g of the sodium salt of the above named final product, $[\alpha]_D^{23}$ −109° C. (c1, pH 7).

EXAMPLE 23

N-[6-[4-(N-Benzyl-L-pyroglutamylamino)phenyl]-1,2-dihydro-2-oxonicotinyl]amoxicillin.

A mixture of 74.5 g (0.5 mol) of L-glutamic acid, 54 g (0.5 mol) of benzaldehyde, 41 g (1.0 mol) of sodium hydroxide, and 1 liter of water was stirred at room temperature for 3 hours. A 5 g portion of 10% palladium on carbon catalyst was added and the mixture hydrogenated for 83 minutes at 51 psig. The catalyst was filtered and the pH of the filtrate was adjusted to 4.2 with 1 N HCl. The solids were filtered, washed with water and dried to give 55.1 g of N-benzyl-L-glutamic acid mp 151°–153° dec., $[\alpha]_D^{23}$ +16° (c4, 1 N HCl). (c 4.1, 1 N HCl). Concentration of the filtrate gave a second crop of 24.9 g, mp 157°–158° dec., $[\alpha]_D^{23}$ +16° (c 4, 1 N HCl).

A 2.37 g portion of N-benzyl-L-glutamic acid was heated to 185°, cooled and the residue crystallized from isopropyl ether to give 0.96 g of N-benzyl-L-pyroglutamic acid mp 91°–93° C., $[\alpha]_D^{23}$ +56° (c4, MeOH). A second crop of 0.56 g, mp 90°–92° C., was obtained by concentrating the filtrate and adding hexane.

A mixture of 3.36 g (15.3 mM) of N-benzyl-L-pyroglutamic acid and 15 ml thionyl chloride was heated at reflux for 2 hours. The reaction mixture was evaporated to an oil and $CH_2Cl_2$ was added and evaporated again. The process was repeated and the oil dissolved in 25 ml of $CH_2Cl_2$ and added to the ice bath cooled silylated derivative of 6-(4-aminophenyl)-1,2-dihydro-2-oxonicotinic acid prepared by the method of Example 1 from 2.76 g (12 mM) of the acid, 4.57 ml (36 mM) of trimethylchlorosilane, 5.04 ml (36 mM) of $Et_3N$, and 90 ml of $CH_2Cl_2$. The reaction mixture was stirred at 5° C. for 3 hours and overnight at room temperature. The $CH_2Cl_2$ was evaporated and water added. The solids were filtered and washed with water, hot methanol, ether, and dried to give 4.77 g of 6-[4-(N-benzyl-L-pyroglutamylamino)phenyl]-1,2-dihydro-2-oxonicotinic acid, $[\alpha]_D^{23}$ −113° (cl, DMSO).

A solution of 4.68 g (10.85 mM) of the above acid, 3.51 g (21.7 mM) carbonyldiimidazole, and 50 ml of DMF was stirred at 49° to 54° C. for 1 hour and at room temperature overnight. Addition of 200 ml of acetonitrile gave a precipitate. The solids were filtered, washed with acetonitrile and ether and dried to afford 3.07 g of the corresponding imidazolide, $[\alpha]_D^{23}$ −103° (cl, DMSO).

A mixture of 4.30 g (6.23 mM) amoxicillin DMSO complex, 3.0 g (6.12 mM) of the above imidazolide, 0.87 ml (6.23 mM) of $Et_3N$, and 50 ml of dimethylacetamide was stirred at 5° C. for 15 minutes and for 2 hours at room temperature. Work up as in Examples 3 and lyophilization of a pH 6.5 solution gave 4.73 g of the sodium salt of the above named final product, $[\alpha]_D^{23}$ +228° (cl, pH 7).

EXAMPLE 24

N-[6-[3-(N-Acetyl-L-alanylamino)phenyl]-1,2-dihydro-2-oxonicotinyl]amoxicillin.

A stirred suspension of 71.3 g (1.32 mol) of sodium methoxide, 500 ml of tetrahydrofuran, and 300 ml of ether was cooled to 0°–5° under nitrogen and a solution of 106.3 g (0.6 mol) of 3-(acetylamino)acetophenone, 96.94 (1.2 mol) of ethyl formate, 700 ml of dry acetonitrile, and 350 ml of tetrahydrofuran was added during 30 min. The reaction was allowed to warm to room temperature with stirring overnight. The organic solvents were decanted from the solids and the solids dissolved in 2.25 l of water. The pH was adjusted to 9.0 with glacial acetic acid and 84.1 g (1.0 mol) of 2-cyanoacetamide was added. The solution was heated at reflux for 3.5 hrs, cooled, and filtered. The solids were washed with water, acetonitrile, and ether and dried to give 93.1 g of 6-(3-acetylaminophenyl)-1,2-dihydro-2-oxonicotinonitrile; mp 326°–328°.

$$E_1^1 \begin{matrix} = 768 \lambda \ 350 \text{ nm} \\ = 890 \lambda \ 242 \text{ nm} \end{matrix} \Big\} \text{ pH 7}$$

A mixture of 92.5 g (0.37 mol) of 6-(3-acetylaminophenyl)-1,2-dihydro-2-oxonicotinonitrile, 185 g of potassium hydroxide, and 740 ml of water was heated at 105° for 30 hrs. The cooled reaction mixture was poured into 285 ml of concentrated hydrochloric acid and ice. The pH of the suspension was adjusted to 5.0 with aqueous sodium hydroxide solution and the solid filtered, washed with water, and dried to give 81.2 g of 6-(3-aminophenyl)-1,2-dihydro-2-oxonicotinic acid.

$$E_1^1 \begin{matrix} = 650 \lambda \ 229 \\ = 825 \lambda \ 227 \end{matrix} \Big\} \text{ pH 7}$$

The silylated derivative of 6-(3-aminophenyl)-1,2-dihydro-2-oxonicotinic acid was prepared by the method of Example 1 from 5.7 g (24.8 mM) of the acid, 10.2 ml (80 mM) of trimethylchlorosilane, 10.4 ml (74.3 mM) $Et_3N$, and 150 ml $CH_2Cl_2$.

A suspension of 6.5 g (49.6 mM) of N-acetyl-L-alanine and 100 ml of acetonitrile was cooled to 5° C. and 5.4 ml (49.6 mM) of N-methylmorpholine was added. The resulting solution was cooled to −20° C. and 3.84 ml (49.6 mM) of methylchloroformate was added. The mixture was stirred at −10°±5° for 1 hour and the above silylated mixture added quickly while maintaining the temperature below −5° C. After the addition was complete, the reaction mixture was stirred at 0° for 1 hour and then allowed to warm to room temperature overnight. The $CH_2Cl_2$ was evaporated and 500 ml of water added. The pH was adjusted to 7.0 with 10% aqueous NaOH and the solution extracted with chloroform (3×500 ml). The pH was brought to 2.0 with 6 N HCl and the precipitated solids filtered, washed with water, suspended in 300 ml of water and lyphilized to afford 7.2 g 6-[3-(N-acetyl-L-alanylamino)phenyl]-1,2-dihydro-2-oxonicotinic acid, $[\alpha]_D^{23}$ −52.2° (cl, pH 7.6).

$$E_1^1 \begin{matrix} = 565 \lambda \ 239 \text{ nm} \\ = 398 \lambda \ 322 \text{ nm} \end{matrix}$$

A solution of 7.2 g (21.0 mM) of the above described acid, 50 ml of DMF, and 7.2 g (44.4 mM) of carbonyldiimidazole was stirred at ambient temperature for 30 minutes and then at 50° to 60° C. for 2 hours. The DMF was evaporated under high vacuum at 45° C. and the residue dissolved in THF. Ether was added and the solvents were decanted from the resulting gum. The gum solidified on trituration with 150 ml of THF. The solids were filtered, washed with THF and ether and dried to give 6.8 g of the corresponding imidazolide.

According to the procedure of Example 5 a mixture of 5.52 g (8 mM) of amoxicillin DMSO complex, 3.0 g (7.6 mM) of the above imidazolide and 40 ml of dimethylacetamide was reacted at room temperature for 3 hours. Work up and lyophilization of the aqueous solution at pH 6.9 gave 4.6 g of the sodium salt of the above named final product, $[\alpha]_D^{23}$ +80.5° (cl, pH 7).

$$E_1^1 \begin{matrix} = 368 \lambda \ 235 \text{ nm} \\ = 266 \lambda \ 349 \text{ nm} \end{matrix}$$

EXAMPLE 25

N-[6-[4-N-Acetyl-4-(acetyloxy)-L-pyrolylamino]phenyl]-1,2-dihydro-2-oxonicotinyl]amoxicillin.

A solution of 100 g (0.76 mol) of L-hydroxyproline and 540 ml of water was cooled to 10° and 297 ml (3.7 mol) of pyridine was added. The temperature was lowered to 5° and 151.2 ml (1.6 mol) of acetic anhydride was slowly added. The reaction was stirred at 0°–5° for 45 min and 81 ml (0.97 mol) of pyridine was added followed by 42.7 ml (0.45 mol) of acetic anhydride. The reaction was stirred overnight in an ice bath allowing the bath to come to room temperature. The reaction was evaporated and the residue was dissolved in ethanol and evaporated to an oily residue. This step was repeated a number of times, and the residue was dissolved in acetone, seeded, and cooled. The white crystals were filtered and recrystallized from ethanol-ether and dried under vacuum at 40° to give 84.8 g of N-acetyl-4-hydroxy-L-proline; mp 124°–131°; $[\alpha]_D^{23}$ −117° (cl, water).

A suspension of 40.0 g (0.173 mol) of 6-(4-aminophenyl)-1,2-dihydro-2-oxonicotinic acid, 72.1 ml (0.517 mol) of triethylamine, and 2800 ml of dichloromethane was stirred at room temperature and 67.8 ml (0.52 mol) of chlorotrimethylsilane was added. The mixture was stirred at room temperature until the solid was almost completely dissolved. A suspension of 63 g (0.362 mol) of N-acetyl-4-hydroxy-L-proline in 650 ml of dichloromethane was cooled to −10° to −15° and 41 ml (0.363 mol) of N-methylmorpholine was added followed by 28.3 ml (0.363 mol) of methyl chloroformate. The reaction was stirred at −15° to −10° for 25 minutes. The reaction temperature was then lowered below −20° and the oxonicotinic acid solution was added in aliquots keeping the temperature below −5°. When the addition was complete, the reaction was stirred in an ice bath overnight, allowing the bath to come to room temperature. The reaction was treated with 30 ml of isopropanol and 30 ml of glacial acetic acid and the resulting mixture was stirred for 10 min at room temperature. The reaction was concentrated and filtered to give 50.1 g of 6-[4-(N-acetyl-4-hydroxy-L-prolyamino)phenyl]-1,2-dihydro-2-oxonicotinic acid; $[\alpha]_D^{23}$ −60.5° (cl, pH 7).

A solution of 29.9 g (0.078 mol) of the above pyridone acid, 120 ml of pyridine, and 60 ml of acetic anhydride was stirred overnight at room temperature. The solution was cooled and upon adding methanol, a precipitate forms. The mixture was cooled and then filtered and the solid was air dried. The solid was recrystallized from 1800 ml of 20% water in methanol and dried at 50° under vacuum to give 21.1 g of 6-[4-[N-acetyl-4-(acetyloxy)-L-prolylamino]phenyl]-1,2-dihydro-2-oxonicotinic acid; $[\alpha]_D^{23}$ +17.3° (cl, 75% DMF/pyridine).

A mixture of 5 g (11.7 mM) of the above oxonicotinic acid, 5 g 30.8 mM) of carbonyldiimidazole, 150 ml of acetonitrile, and 5 ml of N,N-dimethylacetamide was stirred at 50° for 2¾ hours. The solid was filtered, washed with acetonitrile and ether, and dried to give 5.23 g of 6-[4-[N-acetyl-4-(acetyloxy)-L-pyrolylamino]-phenyl]-1,2-dihydro-2-oxonicotinic acid imidazolide.

A solution of 5 g (10.5 mM) of the above imidazolide in 175 ml of N,N-dimethylacetamide was cooled to 5° and 7.7 g (11.5 mM) of amoxicillin dimethyl sulfoxide complex was added. The reaction was stirred at 5° for 3 hrs and 2.92 ml (10.5 mM) of 3.6 M sodium 2-ethylhexanoate in N,N-dimethylacetamide is added. The solution was poured into 450 ml of cold ethyl acetate, and the precipitated solid was filtered, washed with cold ethyl acetate and ether, and dried. The solid was taken up in ice cold water and the pH was adjusted to 2 with dilute hydrochloric acid. The precipitate was filtered, washed with cold water, suspended in cold water, filtered, and washed with cold water. The solid was resuspended in 250 ml of cold water and the pH was adjusted to 6 with dilute sodium hydroxide. The solution was lyophilized to give 7.0 g of the title penicillin as the sodium salt, $[\alpha]_D^{23}$ −383° (cl, pH 7);

$$E_1^1 \quad \begin{matrix} 349 \ \lambda \ 358 \text{ nm} \\ 135 \ \lambda \ 268 \text{ nm} \end{matrix} \quad \text{pH 7}$$

EXAMPLE 26

N-[6-[4-(N-Acetyl-4-oxo-L-pyrolylamino)phenyl]-1,2-dihydro-2-oxonicotinyl]amoxicillin.

Using a literature method [J. Am. Chem. Soc., 79, 185 (1957)] N-acetyl-4-hydroxy-L-proline was converted to N-acetyl-4-oxo-L-proline; $[\alpha]_D^{23}$ −21.3° (c2, MeOH), mp 151°–153°.

A suspension of 8.0 g (34.6 mM) of 6-(4-aminophenyl)-1,2-dihydro-2-oxonicotinic acid, 10 g (99 mM of triethylamine, and 560 ml of dichloromethane was stirred at room temperature for 11.3 g (0.104 mol) of chlorotrimethylsilane was added and solution was observed in 30 min. A suspension of 11.9 g (0.069 mol) of N-acetyl-4-oxo-L-proline in 160 ml of dichloromethane was stirred at −10° and 6.9 g (0.069 mol) of N-methylmorpholine was added followed by 6.6 g (0.069 mol) of methyl chloroformate over a ten min period. The reaction was stirred at −10° for 30 min and cooled to −30°. The above oxonicotinic acid solution was added in aliquots keeping the temperature below −5°, and the reaction mixture was stirred in an ice bath overnight, allowing the bath to come to room temperature. The reaction was evaporated to a gum and water was added. The resulting solid was filtered, dried, and digested with hot ethanol. The purified solid was filtered and dried to give 12 g of 6-[4-(N-acetyl-4-oxo-L-prolylamino)phenyl]-1,2-dihydro-2-oxonicotinic acid;

Using the method of Example 25, the above pyridone acid was converted to to 6-[4-(N-acetyl-4-oxo-L-prolylamino)phenyl]-1,2-dihydro-2-oxonicotinic acid imidazolide.

A solution of 5.3 g (7.9 mM) of amoxicillin dimethyl sulfoxide complex and 15 ml of N,N-dimethylacetamide was stirred at 0°–5° and 3 g (7.2 mM) of the above imidazolide in 5 ml of N,N-dimethylacetamide was added. The reaction was stirred for 2½ hrs at 0°–5° and at room temperature for 1 hour. The reaction is cooled to 0°–5° and 2.2 ml (7.9 mM) of 3.6 M sodium 2-ethylhexanoate in N,N-dimethylacetamide was added and the solution was added to rapidly stirring cold ethyl acetate. The precipitated solid was filtered and washed twice with cold ethyl acetate. The solid was suspended in ether, filtered, washed with ether and air dried. The solid was suspended in ice cold water and the pH was adjusted to 2 with dilute hydrochloric acid. The mixture was centrifuged, and the solid was washed with water, resuspended in cold water and centrifuged again. The solid material was washed with water and suspended in ice cold water. The pH was adjusted to 6.7 with dilute sodium hydroxide and the solution clarified by filtration. The filtrate was lyophilized to give 4.8 of the title penicillin as the sodium salt; $[\alpha]_D^{23}$ −366° (cl, pH 7).

$$E_1^1 \quad \begin{matrix} 354 \ \lambda \ 350 \text{ nm} \\ 145 \ \lambda \ 270 \text{ nm} \end{matrix} \quad \text{pH 7}$$

EXAMPLE 27

N-[6-[4-(N-Acetyl-O-acetylallohydroxy-D-prolylamino)phenyl]-1,2-dihydro-2-oxonicotinyl]amoxicillin.

Using the method of Example 25 for the acetylation of 6-[4-(N-acetyl-4-hydroxy-L-prolylamino)phenyl]-1,2-dihydro-2-oxonicotinic acid, allohydroxy-D-proline [J. Greenstein and M. Wintz, "Chemistry of the Amino Acids", Vol. 3] was converted to N-acetyl-O-acetylallohydroxy-D-proline; $[\alpha]_D^{23}$ +51.6° (cl, H$_2$O).

Using the method of Example 25, 6-(4-aminophenyl)-1,2-dihydro-2-oxonicotinic acid and N-acetyl-O-acetylallohydroxy-D-proline were converted to 6-[4-(N-acetyl-O-acetylallohydroxy-D-prolylamino)-phenyl]-1,2-dihydro-2-oxonicotinic acid; $[\alpha]_D^{23}$ +48.9° (cl, 75% DMF/pyridine).

The above oxonicotinic acid was converted to the 6-[4-(acetyl-O-acetylallohydroxy-D-prolylamino)-phenyl]-1,2-dihydro-2-oxonicotinic acid imidazolide according to the method given in Example 25.

A solution of 3.8 g (5.7 mM) of amoxicillin dimethyl sulfoxide complex and 10 ml N,N-dimethylacetamide was stirred at 0°–5° and a solution of 2.5 g (5.2 mM) of the above imidazolide and 6 ml of N,N-dimethylacetamide was added. The resulting solution is stirred at 0°–5° for 3¼ hrs and at room temperature for 35 min. The reaction mixture was cooled to 0°–5° and 1.58 ml (5.7 mM) 3.6 M sodium 2-ethylhexanoate in N,N-dimethylacetamide was added. The solution was added to 300 ml of rapidly stirring cold ethyl acetate. The resulting precipitate was filtered and washed with cold ethyl acetate. The solid was suspended in ether and the mixture was filtered. The solid was washed with ether and dried under vacuum for 30 min. The dried solid was suspended in 150 ml ice cold water, and the pH was adjusted to 2 with dilute hydrochloric acid. The precipitated solid was filtered, washed with cold water, suspended in cold water, filtered and washed with cold water. The solid was resuspended in 150 ml of ice cold water and the pH was adjusted to 6.2 with dilute sodium hydroxide. The solution was clarified by filtration and the filtrate was lyophilized to give 3.4 g of the title penicillin as the sodium salt; $[\alpha]_D^{23}$ −64° (cl, pH 7).

$E_1^1$ 345 λ 358 nm pH 7

EXAMPLE 28

N-[6-[4-Acetyl-4-(methoxy)-L-prolylamino]phenyl]-1,2-dihydro-2-oxonicotinyl]amoxicillin.

The N-acetyl-4-(methoxy)-L-proline was synthesized from N-acetyl-4-hydroxy-L-proline using a published method [Chem. Pharm. Bull., 12, 725, (1964)]; $[\alpha]_D^{23}$ −62.1° (cl, MeOH).

The synthesis of 6-[4-[N-acetyl-4-(methoxy)-L-prolylamino]phenyl]-1,2-dihydro-2-oxonicotinic acid from N-acetyl-4-(methoxy)-L-proline and 6-(4-aminophenyl)-1,2-dihydro-2-oxonicotinic acid was carried out according to the procedure given in Example 25; $[\alpha]_D^{23}$ +16.3° (cl, DMSO).

The 6-[4-[N-acetyl-4-(methoxy)-L-prolylamino]-phenyl]-1,2-dihydro-2-oxonicotinic acid imidazolide was synthesized from the above oxonicotinic acid using the method given in Example 25.

Reaction of the amoxicillin dimethyl sulfoxide complex and the above imidazolide, as in Example 25, gave 860 mg of the title penicillin as the sodium salt; $[\alpha]_D^{23}$ −36.3 (cl, pH 7).

$$E_1^1 \begin{matrix} 382 \lambda\ 358\ nm \\ 148 \lambda\ 269\ nm \end{matrix} \quad pH\ 7$$

EXAMPLE 29

N-[6-[4-(N-Acetyl-3,4-dehydro-DL-prolylamino)-phenyl]-1,2-dihydro-2-oxonicotinyl]amoxicillin.

A solution of 9.0 g (8.7 mM) of 3,4-dehydro-DL-proline [Chem. and Ind., 583 (1969)] in 50 ml of water was stirred at room temperature and 20 ml of acetic anhydride was added. The solution was stirred for 3 hrs at room temperature and evaporated to an oil which was dissolved in acetone. Upon adding ether, the product precipitates and was filtered to give 11.6 g of N-acetyl-3,4-dehydro-DL-proline.

Using the method of Example 25, 6-(4-aminophenyl)-1,2-dihydro-2-oxonicotinic acid and N-acetyl-3,4-dehydro-DL-proline were converted to 6-[4-(N-acetyl-3,4-dehydro-DL-prolylamino)phenyl-1,2dihydro-2-oxonicotinic acid.

The 6-[4-(N-acetyl-3,4-dehydro-DL-prolylamino)-phenyl]-1,2-dihydro-2-oxonicotinic acid imidazolide was prepared from the above oxonicotinic acid using the method given in Example 25.

Reaction of the amoxicillin dimethyl sulfoxide complex and the above imidazolide under the conditions of Example 25 gave 3.18 g of the title penicillin as the sodium salt; $[\alpha]_D^{23}$ −395° (cl, pH 7).

$$E_1^1 \begin{matrix} 367 \lambda\ 356\ nm \\ 163 \lambda\ 268\ nm \end{matrix} \quad pH\ 7.$$

EXAMPLE 30

N-[6-[4-(N-Acetyl-4-(formyloxy)-L-prolylamino]-phenyl]-1,2-dihydro-2-oxonicotinyl]amoxicillin.

Reaction of 6-[4-(N-acetyl-4-hydroxy-L-prolylamino)phenyl]-1,2-dihydro-2-oxonicotinic acid with formic acid and acetic anhydride gave 6-[4-[N-acetyl-4-(formyloxy)-L-prolyl]amino]phenyl-1,2-dihydro-2-oxonicotinic acid; $[\alpha]_D^{23}$ 19.2° (cl, DMSO).

A suspension of 10.8 g (35 mM) of the above oxonicotinic acid 17.0 g (0.105 mol) of carbonylimidazole, 400 ml of acetonitrile and 20 ml of N,N-dimethylacetamide was stirred at 65° for 2 hours. The solution was concentrated and the yellow precipitate was filtered to give 6.9 g of 6-[4-[N-acetyl-4-(formyloxy)-L-prolyl]amino]phenyl-1,2-dihydro-2-oxonicotinic acid imidazolide.

Reaction of the amoxicillin dimethyl sulfoxide complex and the above imidazolide under the conditions of Example 25 gave 1.21 g of the title penicillin as the sodium salt; $[\alpha]_D^{23}$ −366° (cl, pH 7).

$$E_1^1 \begin{matrix} 363 \lambda\ 358\ nm \\ 147 \lambda\ 268\ nm \end{matrix} \quad pH\ 7$$

EXAMPLE 31

N-[6-[4-[N-Acetyl-4-(1-oxopropxy)-L-prolylamino]-phenyl]-1,2-dihydro-2-oxonicotinyl]amoxicillin A suspension of 4 g (10.4 mM) of 6-[4-(N-acetyl-4-hydroxy-L-prolylamino)phenyl]-1,2-dihydro-2-oxonicotinic acid, 4 ml (31 mM) of propionic anhydride, and 25 ml of pyridine was stirred at room temperature for 1 hr. The resulting solution was allowed to stand overnight at room temperature and methanol was added. The solid was filtered, washed, and dried to give 2.2 g of 6-[4-[N-acetyl-4-(1-oxopropoxy)-L-prolylamino]phenyl]-1,2-dihydro-2oxonicotinic acid. Another 2.0 g were obtained by evaporating the filtrate and treating the residue with water. The pH was adjusted to 2.5 with 1 N hydrochloric acid and cooled and the solid was filtered, washed with water and air dried.

A mixture of 2.2 g (5 mM) of the above pyridone acid, 2.2 g (13.5 mM) of carbonyldiimidazole, 70 ml of acetonitrile, and 2 ml of dimethylformamide was stirred at 55° for 1.5 hour and at room temperature for 4.5 hrs. The solid was filtered, washed with acetonitrile and ether and dried to give 2.02 g of 6-[4-[N-acetyl-4-(1-oxopropoxy-L-prolylamino]phenyl]-1,2-dihydro-2-oxonicotinic acid imidazolide.

A suspension of 3.92 (6.3 mM) of amoxicillin dimethyl sulfoxide complex, 2.81 g (5.7 mM) of the above imidazolide, and 22 ml of N,N-dimethylacetamide was stirred at 0°-5° for 2 hrs and 1.75 ml (5.7 mM) of 3.3 M sodium 2-ethylhexamoate in N,N-dimethylacetamide was added. The solution was poured into 300 ml of stirring ethyl acetate and the precipitated solid was filtered, washed with ethyl acetate and ether, and dried to give 5.1 g of crude sodium salt. The solid was dissolved in 200 ml of ice water and the pH was adjusted to 2.5 with 1 N hydrochloric acid. The precipitate was filtered, washed with water and resuspended in ice water and dissolved by adjusting the pH to 5.8 with 1 N sodium hydroxide. The solution was clarified by filtration and lyophilized to give 4.6 g of the title penicillin as the sodium salt; $[\alpha]_D^{23}$ −337° (cl, pH 7)

$E_1^1$ 350 λ 358 nm pH 7

EXAMPLE 32

N-[6-[4-(N-Methyl-5-oxo-L-prolyl)amino]-phenyl-1,2-dihydro-2-oxonicotinyl]amoxicillin A suspension of 3.09 g (21.6 mM) of N-methyl-5-oxo-L-proline, 1.58 ml (21.6 mM) thionyl chloride, 1.67 ml (21.6 mM) dimethylformamide, and 50 ml of dichloromethane was stirred with ice bath cooling for 70 min. Simultaneously, a suspension of 3.31 g (14.4 mM) of 6-(4-aminophenyl)-1,2-dihydro-2-oxonicotinic acid, 100 ml dichloromethane, 6.05 ml (43.2 mM) triethylamine, and 5.48 ml (4.32 mM) chlorotrimethylsilane was stirred at room temperature for 1 hour. The silylated mixture was cooled with an ice bath and the acid chloride complex was added. The reaction mixture was stirred in an ice bath for 6 hrs and at room temperature overnight. The reaction mixture was treated with 50 ml of 2-propanol and was filtered to give 3.70 g of 6-[4-(N-methyl-5-oxo-L-prolyl)amino]phenyl-1,2-dihydro-2-oxonicotinic acid; $[\alpha]_D^{23}$ +11.8° (cl, DMSO).

A suspension of 3.44 g (9.68 mM) of the above pyridone acid, 3.14 g (19.36 mM) of carbonyldimidazole, and 35 ml of dimethylformamide was stirred at 53°-57° for 45 min and at room temperature overnight. After addition of 100 ml of acetonitrile, the solid was collected by filtration. The solid was washed with acetonitrile and ether to give 2.51 g of 6-[4-(N-methyl-5-oxo-L-prolyl)amino]phenyl-1,2-dihydro-2-oxonicotinic acid imidazolide; $[\alpha]_D^{23}$ +9.8° (cl, DMSO).

A mixture of 2.46 g (6.07 mM) of the above imidazolide, 4.18 g (6.07 mM) of amoxicillin dimethyl sulfoxide complex, 0.85 ml (6.07 mM) of triethylamine, and 50 ml of N,N-dimethylacetamide was stirred at 0°-5° for 30 min at room temperature for 2½ hrs. The reaction solution was poured into ice and water and acidified to pH 2 with 1 N hydrochloric acid. The solid was filtered, washed with water, stirred with water, and refiltered. The filtrate was suspended in 150 ml water and the pH was adjusted to 6.5 with 1 N sodium hydroxide with cooling. The solution was filtered and lyophilized to give 3.6 g of the sodium salt of the title penicillin; $[\alpha]_D^{23}$ +54° (cl, pH 7).

$$E_1^1 \begin{array}{c} 384 \; \lambda \; 358 \text{ nm} \\ 156 \; \lambda \; 269 \text{ nm} \end{array} \text{pH 7}$$

EXAMPLE 33

N-[6-[4-(N,N'-Diacetyl-L-lysylamino)phenyl]-1,2-dihydro-2-oxonicotinyl]amoxicillin A solution of 29.0 g (70 mM) of N,N'-bis(benzyloxycarbonyl)-L-lysine [Helv. Chem. Acta, 41, 1778 (1958)] in 200 ml of dichloromethane was stirred at −10° and 7.2 g (70 mM) of N-methylmorpholine is added. The temperature was lowered to −14° and 9.55 g (70 mM) of isobutyl chloroformate was added dropwise over a period of 10 min and stirring was continued at −14° to −11° for 40 min. A suspension of 8.0 g (35 mM) of 6-(4-aminophenyl)-1,2-dihydro-2-oxonicotinic acid, 10.5 g (35 mM) of triethylamine and 200 ml of dichloromethane was stirred at 5° and 12.0 g (35 mM) of chlorotrimethylsilane was added. After 1 hr at room temperature this solution was added over a period of 30 min at −12° to −14° to the mixed anhydride formed above. After 3 hrs at 0°, the solution was allowed to stir overnight at room temperature. The reaction mixture was filtered and the filtrate was stirred with 15 ml of isopropanol for 30 min. The resulting yellow precipitate was filtered, washed, and dried to give 16.6 g of 6-[4-(N,N'-diacetyl-L-lysylamino)phenyl]-1,2-dihydro-2-oxonicotinic acid; mp 199°-200°, $[\alpha]_D^{23}$ +24.2° (cl, DMSO).

A solution of hydrogen bromide in glacial acetic acid (30%, 60 ml) was stirred at room temperature and 16.3 g (26 mM) of the above pyridone acid was added over 10 min and stirring continued for 15 min. A solid separates from the solution during a 2 hr period, and the mixture was diluted with 300 ml of ethyl acetate. The mixture was stirred for 2 hrs and filtered giving 10.9 g of 6-[4-(L-lysylamino)phenyl]-1,2-dihydro-2-oxonicotonic acid dihydrobromide as yellow crystals, mp 291°-292° dec; $[\alpha]_D^{23}$ +39.4° (cl, DMSO).

An aqueous solution of the above dihydrobromide was stirred at room temperature and 75 ml of concentrated ammonium hydroxide was added. The yellow crystalline precipitate was filtered after stirring for 2 hrs to give 6.9 g of 6-[4-(L-lysylamino)phenyl]-1,2-dihydro-2-oxonicotinic acid; mp 281°-282° dec; $[\alpha]_D^{23}$ +41.5° (cl, pH 7).

The above pyridone acid (6.7 g, 18.7 mM) was suspended in 60 ml of water and treated with 10 ml of acetic anhydride with stirring. After 3 min a yellow precipitate begins to separate from the solution. Another 2.5 ml of acetic anhydride was added and stirring was continued for 4 hrs at room temperature. The solid was filtered, washed, and dried to give 7.8 g of 6-4[-(N,N'-diacetyl-L-lysylamino)phenyl]-1,2-dihydro-2-oxonicotinic acid; mp 263°-264° dec; $[\alpha]_D^{23}$ −63° (cl, pyridine).

A suspension of 7.3 g (16.5 mM) of the above pyridone acid, 5.4 g (33 mM) of carbonyldiimidazole, and in 75 ml of N,N-dimethylformamide was stirred at 55° for 40 min and overnight at room temperature. Acetonitrile (350 ml) was added dropwise over 30 min and the resulting precipitate was stirred for 2.5 hrs. The solid was filtered and washed with 100 ml of acetonitrile to give 7.4 g of 6-[4-(N,N'-diacetyl- L-lysylamino)phenyl]-1,2-dihydro-2-oxonicotinic acid imidazolide; mp 219°-220° dec., $[\alpha]_D^{23}$ +21° (cl, DMSO). A suspension of 6.7 g (10 mM) of amoxicillin dimethyl sulfoxide complex, 4.5 g (9.13 mM) of the above imidazolide, and 50 ml of dry N,N-dimethylacetamide was stirred at room temperature for 3 hrs. The solution was cooled to 0° and was treated with 4 ml (14.3 mM) of 3.6 M sodium 2-ethylhexanoate in N,N-dimethylacetamide. The resulting solution was stirred and 350 ml of ethyl acetate was added over a period of 30 min. The precipitated solid was collected, washed with 100 ml of ethyl acetate, and with 100 ml of ether. The solid was dissolved in 150 ml of ice water and acidified with 1 N hydrochloric acid to pH 2.0. The resulting solid was collected and washed with 300 ml of ice cold water. The solid was suspended in 100 ml of water and the pH was adjusted to 6.5 with 1 N sodium hydroxide at 5°. The solution was filtered and the filtrate was lyophilized to give 6.8 g of the title penicillin as the sodium salt; $[\alpha]_D^{23}$ +174° (cl, DMSO).

$$E_1^1 \quad \begin{array}{c} 137 \lambda\ 268\ nm \\ 335 \lambda\ 357\ nm \end{array} \quad pH\ 7$$

EXAMPLE 34

N-[6-[4-[(2-Oxo-1-pyrrolidinyl)acetylamino]-phenyl]-1,2-dihydro-2-oxonicotinyl]amoxicillin A suspension of 4.29 g (30 mM) of 2-oxo-1-pyrrolidineacetic acid, 2.20 ml (30 mM) of thionyl chloride, 2.32 ml (30 mM) of dimethylformamide, and 75 ml of dichloromethane was stirred with ice bath cooling for 1¼ hrs. A mixture of 4.60 g (20 mM) of 6-(4-aminophenyl)-1,2-dihydro-2-oxonicotinic acid, 140 ml of dichloromethane, 8.4 ml (60 mM) of triethylamine, and 7.6 ml (60 mM) of chlorotrimethylsilane was stirred at room temperature for 1 hr. The silylated pyridone solution was cooled with an ice bath and the cold solution of the acid chloride was added. The reaction mixture was stirred for 4 hrs with cooling and at room temperature for 18 hrs. The reaction mixture was evaporated to a wet solid. Ethanol was added, and the mixture was evaporated. The residue was treated with water and the solid filtered. The solid was washed with water, ethanol, and ether and dried to give 6.49 g of 6-[4-[2-oxo-1-pyrrolidinyl)acetylamino]-phenyl]-1,2-dihydro-2-oxonicotinic acid; mp <320°.

A mixture of 5.71 g (15.67 mM) of the above pyridone acid, 5.08 g (31.34 mM) of carbonyldiimidazole, and 75 ml of dimethylformamide was stirred at 50°-55° for 1¼ hrs and at room temperature for 16 hrs. The mixture was diluted with 100 ml of acetonitrile and filtered. The solid was washed with acetonitrile and ether to give 4.80 g of 6-[4-[(2-oxo-1-pyrrolidinyl)acetylamino]-phenyl]-1,2-dihydro-2-oxonicotinic acid imidazolide.

A suspension of 4.80 g (11.8 mM) of the above imidazolide, 8.13 g (11.8 mM) amoxicillin dimethyl sulfoxide complex, 100 ml of N,N-dimethylacetamide, and 1.65 ml (11.8 mM) of triethylamine was stirred in an ice bath for 30 min and at room temperature for 2½ hrs. The reaction solution was poured into 500 ml of ice and water and acidified to pH 2.5 with 1 N hydrochloric acid. The resulting mixture was centrifuged, the liquid was decanted and water added and centrifuged again. The liquid was decanted and the wet solid was suspended in water and dissolved by adjusting the pH to 6.5 with 1 N sodium hydroxide. The solution was filtered and lyophilized to give 6.82 g of the title penicillin as the sodium salt $[\alpha]^{23}$ −295° (cl, pH 7).

$$E_1^1 \quad \begin{array}{c} 340 \lambda\ 358\ nm \\ 312 \lambda\ 268\ nm \end{array} \quad pH\ 7$$

We claim:

1. A compound of the formula

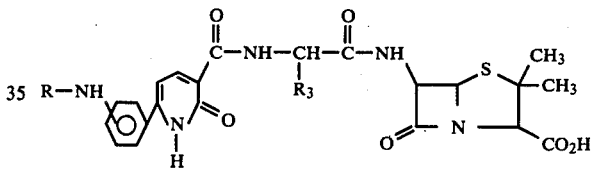

and pharmaceutically acceptable salts thereof; wherein R is

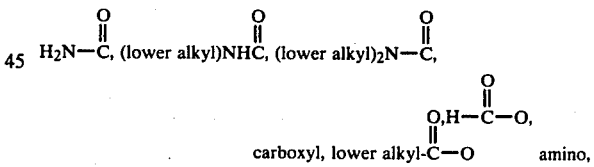

or $R_1$-[$NR_4$-acyl]$_n$; x is an integer from one to five, x' is zero, one or two; $R_1$ is hydrogen, lower alkyl, benzyl, or

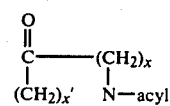

wherein $R_2$ is hydrogen, amino or a lower alkyl group of from one to four carbon atoms, optionally substituted by from one to three chlorine or fluorine atoms; $R_4$ is hydrogen or lower alkyl; N-acyl is an aminoacyl moiety derived from a carboxylic acid of from two to ten carbon atoms optionally substituted by from one to three of the following groups, formamido, lower alkylamido, hydroxyl,

carbamido, carbonyl oxygen, lower alkoxy, lower alkylthio, or sulfonic acid; $R_3$ is phenyl, 4-hydroxyphenyl, 2-thienyl or cyclohexa-1,4-dien-1-yl and n is an integer of from one to four.

2. A compound of claim 1 wherein R-NH is in the p position and R-NH is an optically active fragment in the L form.

3. A compound of claim 1 wherein NH-acyl is L-alanyl, L-glutaminyl, L-4-hydroxyprolyl, L-prolyl, L-pyroglutamyl, γ-aminobutyryl, β-alanyl or L-valyl; $R_2$ is a carbon fragment of from one to four carbon atoms and $R_3$ is phenyl or p-hydroxyphenyl.

4. A compound of claim 1 having the name N-[6-[4-(N-acetyl-L-alanylamino)phenyl]-1,2-dihydro-2-oxonicotinyl]amoxicillin and pharmaceutically acceptable salts thereof.

5. A compound of claim 1 having the name N-[6-[4-(N-acetylglycylamino)phenyl]-1,2-dihydro-2-oxonicotinyl]-amoxicillin and pharmaceutically acceptable salts thereof.

6. A compound of claim 1 having the name N-[6-[4-(N-acetyl-DL-alanylamino)phenyl]-1,2-dihydro-2-oxonicotinyl]amoxicillin and pharmaceutically acceptable salts thereof.

7. A compound of claim 1 having the name N-[6-[4-(N-dichloroacetyl-L-alanylamino)phenyl]-1,2-dihydro-2-oxonicotinyl]amoxicillin and pharmaceutically acceptable salts thereof.

8. A compound of claim 1 having the name N-[6-[4-(N-carbamido-L-alanylamino)phenyl]-1,2-dihydro-2-oxonicotinyl]amoxicillin and pharmaceutically acceptable salts thereof.

9. A compound of claim 1 having the name N-[6-[4-(L-alanylamino)phenyl]-1,2-dihydro-2-oxonicotinyl]-amoxicillin and pharmaceutically acceptable salts thereof.

10. A compound of claim 1 having the name N-[6-[4-(N-acetyl-γ-aminobutyrylamino)phenyl]-1,2-dihydro-2-oxonicotinyl]amoxicillin and pharmaceutically acceptable salts thereof.

11. A compound of claim 1 having the name N-[6-[4-(N-acetyl-L-isoleucylamino)phenyl]-1,2-dihydro-2-oxonicotinyl]amoxicillin and pharmaceutically acceptable salts thereof.

12. A compound of claim 1 having the name N-[6-[4-(N-acetyl-D-asparaginylamino)phenyl]-1,2-dihydro-2-oxonicotinyl]amoxicillin and pharmaceutically acceptable salts thereof.

13. A compound of claim 1 having the name N-[6-[4-(N-acetyl-DL-prolylamino)phenyl]-1,2-dihydro-2-oxonicotinyl]amoxicillin and pharmaceutically acceptable salts thereof.

14. A compound of claim 1 having the name N-[6-[4-(N-acetyl-L-prolylamino)phenyl]-1,2-dihydro-2-oxonicotinyl]amoxicillin and pharmaceutically acceptable salts thereof.

15. A compound of claim 1 having the name N-[6-[4-(N-acetyl-L-glutaminylamino)phenyl]-1,2-dihydro-2-oxonicotinyl]amoxicillin and pharmaceutically acceptable salts thereof.

16. A compound of claim 1 having the name N-[6-[4-(N-trifluoroacetylglycylamino)phenyl]-1,2-dihydro-2-oxonicotinyl]amoxicillin and pharmaceutically acceptable salts thereof.

17. A compound of claim 1 having the name N-[6-[4-(N-trifluoracetyl-alpha-aminoisobutyrylamino)phenyl]-1,2-dihydro-2-oxonicotinyl]amoxicillin and pharmaceutically acceptable salts thereof.

18. A compound of claim 1 having the name N-[6-[4-(N-acetyl-alpha-aminoisobutyrylamino)phenyl]-1,2-dihydro-2-oxonicotinyl]amoxicillin and pharmaceutically acceptable salts thereof.

19. A compound of claim 1 having the name N-[6-[4-(N-acetyl-L-cysteiylamino)phenyl]-1,2-dihydro-2-oxonicotinyl]amoxicillin and pharmaceutically acceptable salts thereof.

20. A compound of claim 1 having the name N-[6-[4-(N-acetyl-L-serylamino)phenyl]-1,2-dihydro-2-oxonicotinyl]amoxicillin and pharmaceutically acceptable salts thereof.

21. A compound of claim 1 having the name N-[6-[4-(N-acetyl-L-hydroxyprolylamino)phenyl-1,2-dihydro-2-oxonicotinyl)amoxicillin and pharmaceutically acceptable salts thereof.

22. A compound of claim 1 having the name N-[6-[4-(N-formyl-L-alanylamino)phenyl]-1,2-dihydro-2-oxonicotinyl]amoxicillin and pharmaceutically acceptable salts thereof.

23. A compound of claim 1 having the name N-[6-[4-(N-acetyl-L-alanyl-L-alanylamino)phenyl]-1,2-dihydro-2-oxonicotinyl]amoxicillin and pharmaceutically acceptable salts thereof.

24. A compound of claim 1 having the name N-[6-[4-(L-pyroglutamylamino)phenyl]-1,2-dihydro-2-oxonicotinyl]amoxicillin and pharmaceutically acceptable salts thereof.

25. A compound of claim 1 having the name N-[6-[4-(N,N'-diacetyl-DL-lysylamino)phenyl]-1,2-dihydro-2-oxonicotinyl]amoxicillin and pharmaceutically acceptable salts thereof.

26. A compound of claim 1 having the name N-[6-[4-(N-benzyl-L-pyroglutamylamino)phenyl]-1,2-dihydro-2-oxonicotinyl]amoxicillin and pharmaceutically acceptable salts thereof.

27. A compound of claim 1 having the name N-[6-[3-(N-acetyl-L-alanylamino)phenyl]-1,2-dihydro-2-oxonicotinyl]amoxicillin and pharmaceutically acceptable salts thereof.

28. A compound of claim 1 having the name N-[6-[4-N-acetyl-4-(acetyloxy)-L-prolylamino]phenyl]-1,2-dihydro-2-oxonicotinyl]amoxicillin and pharmaceutically acceptable salts thereof.

29. A compound of claim 1 having the name N-[6-[4-(N-acetyl-4-oxo-L-prolylamino)phenyl]-1,2-dihydro-2-oxonicotinyl]amoxicillin and pharmaceutically acceptable salts thereof.

30. A compound of claim 1 having the name N-[6-[4-(N-acetyl-O-acetylallohydroxy-D-prolylamino)-phenyl]-1,2-dihydro-2-oxonicotinyl]amoxicillin and pharmaceutically acceptable salts thereof.

31. A compound of claim 1 having the name N-[6-[N-acetyl-4-(methoxy)-L-prolylamino]phenyl]-1,2-dihydro-2-oxonicotinyl]amoxicillin and pharmaceutically acceptable salts thereof.

32. A compound of claim 1 having the name N-[6-[4-(N-acetyl-3,4-dehydro-DL-prolylamino)-phenyl]-1,2-dihydro-2-oxonicotinyl]amoxicillin and pharmaceutically acceptable salts thereof.

33. A compound of claim 1 having the name N-[6-[4-[N-acetyl-4-(formyloxy)-L-prolylamino]-phenyl]-1,2- dihydro-2-oxonicotinyl]amoxicillin and pharmaceutically acceptable salts thereof.

34. A compound of claim 1 having the name N-[6-[4-[N-acetyl-4-(1-oxopropoxy)-L-prolylamino]-phenyl]-1,2-dihydro-2-oxonicotinyl]amoxicillin and pharmaceutically acceptable salts thereof.

35. A compound of claim 1 having the name N-[6-[4-(N-methyl-5-oxo-L-prolyl)amino]phenyl-1,2-dihydro-2-oxonicotinyl]amoxicillin and pharmaceutically acceptable salts thereof.

36. A compound of claim 1 having the name N-[6-[4-(N,N'-diacetyl-L-lysylamino)phenyl]-1,2-dihydro-2-oxonicotinyl]amoxicillin and pharmaceutically acceptable salts thereof.

37. A compound of claim 1 having the name N-[6-[4-[(2-oxo-1-pyrrolidinyl)acetylamino]phenyl]-1,2-dihydro-2-oxonicotinyl]amoxicillin and pharmaceutically acceptable salts thereof.

38. An antibacterial pharmaceutical composition comprising from 50 mg to 1000 mg of a compound of claim 1 and a pharmaceutical carrier.

39. A method for treating bacterial infections which comprises administering 5 mg to 100 mg per kg of body weight per day of the pharmaceutical composition of claim 38 to a mammal having a bacterial infection.

* * * * *